US011122778B2

(12) United States Patent
Haase et al.

(10) Patent No.: US 11,122,778 B2
(45) Date of Patent: Sep. 21, 2021

(54) AUTOMATED NONINVASIVE DETERMINING THE SEX OF AN EMBRYO AND THE FERTILITY OF A BIRD'S EGG

(71) Applicant: TECHNISCHE UNIVERSITÄT MÜNCHEN, Munich (DE)

(72) Inventors: Axel Haase, Rimpar (DE); Benjamin Michael Schusser, Freising (DE); Miguel Molina-Romero, Munich (DE); Pedro A. Goméz, Munich (DE); Maximilian Aigner, Velden (DE); Stephan Huber, Munich (DE); Alexander Joos, Lörrach (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 16/760,828

(22) PCT Filed: Nov. 13, 2018

(86) PCT No.: PCT/EP2018/081019
§ 371 (c)(1),
(2) Date: Apr. 30, 2020

(87) PCT Pub. No.: WO2019/092265
PCT Pub. Date: May 16, 2019

(65) Prior Publication Data
US 2020/0281166 A1  Sep. 10, 2020

(30) Foreign Application Priority Data
Nov. 13, 2017 (EP) .................................... 17201373

(51) Int. Cl.
*A01K 43/04* (2006.01)
*B07C 5/344* (2006.01)
(Continued)

(52) U.S. Cl.
CPC .............. *A01K 43/04* (2013.01); *B07C 5/344* (2013.01); *G01N 24/085* (2013.01); *G01N 33/08* (2013.01);
(Continued)

(58) Field of Classification Search
CPC ...... A01K 43/04; B07C 5/344; G01N 24/085; G01N 33/08; G01R 33/3415;
(Continued)

(56) References Cited

U.S. PATENT DOCUMENTS 6,029,080 A * 2/2000 Reynnells .............. G01N 33/08
   600/407
6,149,956 A  11/2000 Boerjan
(Continued)

FOREIGN PATENT DOCUMENTS

EP        0890838 A1    1/1999
RU     2 436 296 C2    3/2010
(Continued)

OTHER PUBLICATIONS

International Searching Authority/European Patent Office, International Search Report and Written Opinion of the International Searching Authority, Application No. PCT/EP2018/081019, dated Feb. 12, 2019, 16 pages.
(Continued)

*Primary Examiner* — Dixomara Vargas
(74) *Attorney, Agent, or Firm* — Sunstein LLP

(57) ABSTRACT

Disclosed herein is a method of automated noninvasive determining the sex of an embryo of a bird's egg (14) as well as a corresponding apparatus. The method comprises the following steps: conveying a plurality of bird eggs (14) sequentially or in parallel into an NMR apparatus (18), subjecting the bird eggs (14) to an NMR measurement, to thereby determine, for each of said eggs (14), one or more
(Continued)

NMR parameters associated with the egg (14) selected from the group consisting of a Ti relaxation time, a T2 relaxation time and a diffusion coefficient, forwarding said one or more NMR parameters, or parameters derived therefrom, to a classification module (38), said classification module (38) configured for determining, based on said one or more NMR parameters or parameters derived therefrom, a prediction of the sex of the embryo of the associated egg (14), and conveying said plurality of bird eggs (14) out of said NMR apparatus (18) and sorting the eggs (14) according to the sex prediction provided by said classification module (38).

23 Claims, 9 Drawing Sheets

(51) Int. Cl.
G01N 24/08 (2006.01)
G01N 33/08 (2006.01)
G01R 33/3415 (2006.01)
G01R 33/56 (2006.01)
G01R 33/561 (2006.01)
G01R 33/30 (2006.01)

(52) U.S. Cl.
CPC ....... G01R 33/307 (2013.01); G01R 33/3415 (2013.01); G01R 33/561 (2013.01); G01R 33/5608 (2013.01); G01R 33/5611 (2013.01)

(58) Field of Classification Search
CPC .............. G01R 33/5608; G01R 33/561; G01R 33/307; G01R 33/5611
See application file for complete search history.

(56) References Cited

U.S. PATENT DOCUMENTS

| 8,486,690 | B2* | 7/2013 | Burns | G01R 33/465 |
| | | | | 435/286.5 |
| 9,835,560 | B2* | 12/2017 | Galli | G01N 21/65 |
| 10,852,284 | B2* | 12/2020 | Steiner | A01K 41/00 |
| 2006/0279281 | A1 | 12/2006 | Rapoport | |
| 2009/0165723 | A1 | 7/2009 | Moran | |
| 2015/0260704 | A1 | 9/2015 | Bruins et al. | |
| 2016/0057977 | A1 | 3/2016 | Sewiolo et al. | |
| 2019/0383782 | A1* | 12/2019 | Steiner | G01N 21/6408 |
| 2020/0348248 | A1* | 11/2020 | Gomez | G01R 33/307 |

FOREIGN PATENT DOCUMENTS

RU 2008 137 794 A 3/2010
RU 2 612 370 C1 3/2017

OTHER PUBLICATIONS

A. Davenel et al., *Attempts for early gender determination of chick embryos in ovo using Magnetic Resonance Imaging*, Jun 1, 2005, http://www.wpsa.com/index.php/publications/wpsa-proceedings/2015/xxii-european-symposium-on-the-quality-of-poultry-meat-and-the-xvi-european-symposium-on-the-quality-of-eggs-and-egg-products/2196-attempts-for-early-gender-determination-of-chick-embryos-in-ovo-using-magnetic-resonance-imaging/file [retrieved on Mar. 23, 2018], 4 pages.

S. Klein et al., *Localization of the fertilized germinal disc in the chicken egg before incubation*, Poultry Science, vol. 81, No. 4, Apr. 1, 2002, pp. 529-536 XP055461661.

* cited by examiner

AUTOMATED NONINVASIVE DETERMINING THE SEX OF AN EMBRYO AND THE FERTILITY OF A BIRD'S EGG

CROSS-REFERENCE TO RELATED APPLICATIONS

This application is the national phase entry of International Patent Application No. PCT/EP2018/081019 filed on Nov. 13, 2018, and claims the benefit of EP Patent Application No. 17201373.2 filed Nov. 13, 2017, the disclosures of which are incorporated herein by reference in their entirety.

FIELD OF THE INVENTION

The present invention is in the field of chicken farming for the production of egg laying hens and poultry. More particularly, in one aspect the present invention relates to a method and an apparatus for noninvasive determining the sex of an embryo of a bird's egg, in particular a chicken egg. In another aspect, the present invention relates to a method and an apparatus for noninvasive determining the fertility of a bird's egg, in particular a chicken egg.

BACKGROUND OF THE INVENTION

In year 2015, about 1338 billion chicken eggs were produced. Chickens farmed for egg production are called egg laying hens. Some hen breeds can produce over 300 eggs per year. When rearing egg laying hens, shortly after hatching, the sex of the chicken is determined, and only the hens are raised. While the roosters could in principle be also raised and used for meat production, the specific egg laying breeds are significantly inferior for this purpose as compared to specific meat production breeds, as meat production breeds will provide for a higher daily gain of weight, a higher final weight and a more favorable distribution of meat on the body. This means that currently, in the rearing of egg laying hens, roosters are culled shortly after hatching. This procedure is found morally inappropriate by many, and is in conflict with current and probably even more with future animal protection law. In particular, it is against the law in most countries, including Germany, to give pain, suffering or damage to animals without just cause, and there is ongoing debate as to what extent this is violated when culling roosters after hatching.

In order to alleviate this problem, there have been attempts to determine the sex of a chicken prior to hatching. For example, using molecular biologic methods, it is possible to carry out a PCR specifically for the female W chromosome, and based on a specific amplicon for the W chromosome, female animals can be identified. In principle, it is possible to carry out these molecular biological methods even in ovo, but this would imply that a tissue sample of the embryo would need to be taken, and in any case, the shell would need to be damaged.

In addition to the molecular biological determination of the sex in ovo, there have been attempts to determine the sex based on the content of sexual hormones in the allantois liquid of the embryos, as demonstrated in Weissmann, A., Reitemeier, S., Hahn, A., Gottschalk, J. & Einspanier, A. *Sexing domestic chicken before hatch: A new method for in ovo gender identification*, and in *Theriogenology* 80, 199-205 (2013), Tran, H. T., Ferrell, W. & Butt, T. R. *An estrogen sensor for poultry sex sorting. J. Anim. Sci.* 88, 1358-1364 (2010). Based on a difference in the estrone sulfate concentration, it was found to be possible to distinguish between male and female chicken embryos. However, this method comes with a number of problems. For example, the hatching rate is found to drop as a consequence of taking the samples of the allantois liquid, which is presumably due to the hole that needs to be formed in the egg shell. Moreover, with this method, the sex can only be determined between the 4th and the loth day of the embryo.

A noninvasive possibility to determine the sex of the chicken in ovo is based on sex specific feather colors. Using hyperspectral methods, it is possible to determine the color of the feathers through the egg shell and to thereby determine the sex, as is demonstrated in Göhler, D., Fischer, B. & Meissner, S. *In-ovo sexing of 14-day-old chicken embryos by pattern analysis in hyperspectral images (VIS/NIR spectra): A non-destructive method for layer lines with gender specific down feather color. Poult. Sci.* 96, 1-4 (2017). While this method looks very advantageous at first sight, it requires rearing of special chicken breeds having sex specific feather markers. This technique can therefore not be universally applied to all chicken breeds.

A further optical method for use in the determination of sex in ovo is based on Raman spectroscopy. This method has already been successfully applied to chicken after hatching, where the sex has been determined based on feather follicles, see Harz, M. et al. *Minimal Invasive Gender Determination of Birds by Means of UV-Resonance Raman Spectroscopy. Anal. Chem.* 80, 1080-1085 (2008). For this spectroscopic method, light in the UV range was used, which unfortunately bears the risk of photo toxic effects. In Galli, R. et al. *In ovo sexing of domestic chicken eggs by Raman spectroscopy, Anal. Chem.* 88, 8657-8663 (2016), IR radiation was used for determining the sex in ovo. For this purpose, the egg shell was opened using a $CO_2$ laser, providing access to the chicken embryo on day 3-5. The measurement was performed directly at a blood vessel of the embryo. The average differences in the Raman spectroscopy signals were found to be larger for male embryos than for female embryos, which allows for determining the sex. The hatching rate of chicken subjected to such measurement based on Raman spectroscopy was only slightly lower than usual, and no negative influence on the further development of the chicken could be observed.

In Galli, R. et al. *In ovo sexing of chicken eggs by fluorescence spectroscopy. Anal. Bioanal. Chem.* 409, 1185-1194 (2017), fluorescence spectroscopy is used to determine the sex of chicken embryos. In this case too, it was found possible to determine the sex on day 3.5 of the embryo based on a pronounced fluorescence signal at 910 nm for male embryos. By combining the data of fluorescence and Raman spectroscopy, the sex could be determined correctly in 90% of the cases. However, this method still requires opening the egg shell, in order to gain access to the embryo's blood vessels. This bears the risk of contamination and a smaller hatching rate.

DE 10 2013 205 426 A1 discloses a method for determining the sex of an embryo in an egg in a noninvasive manner, by determining the concentration of estradiol, and optionally in addition the concentration of testosterone. In one embodiment, the concentration of estradiol is determined by means of NMR spectroscopy, based on a chemical shift. The concentration of estradiol is determined prior to the $25^{th}$ day of breeding, and preferably on the $17^{th}$ day of breeding. However, this method has not found its way to a practical application. A difficulty with this method is that the concentrations of hormones are typically in a range of pMol/l only and can therefore not be reliably detected with NMR spectroscopy.

WO 00/01302 describes a non-invasive method and apparatus for sexing chicken in the egg. The method employs high-resolution NMR imaging for determining whether the embryo within the egg contains male or female sex organs. Indeed, for this method, imaging with a spatial resolution of higher than 0.1 mm is needed to determine male and female sex organs. Such a high resolution is not compatible with short measuring times necessary for practical applications. Moreover, very high-resolution images at late states of incubation are very sensitive to motion and hence suffer from distortions.

Accordingly, none of these two methods based on NMR spectroscopy or NMR imaging have found to be practicably feasible.

Moreover, in the poultry industry it is also desired to noninvasively determine the fertility of an egg. The poultry industry is one of the most important sources of animal protein for human consumption. The magazine *Poultry Trends* 2016 estimates that the worldwide production and consumption of poultry meat will increase by 20% by 2025, to over 130 million metric tons. In 2016, the global market already produced 116.4 million metric tons of poultry meat, where the top 185 poultry producing companies slaughtered close to 38 billion heads to satisfy global demand. In the United States alone, the poultry industry was valued at $38.7 billion USD.

Despite its significant volume, the process of incubating eggs to hatch poultry is far from perfect. An average poultry facility only hatches 75%-85% of the eggs it incubates. The other 15-25% of eggs either undergo early embryonic death or are not fertile. Currently, infertile and dead embryos are separated from live embryos after 18 days of incubation with non-invasive technologies, such as the Embrex® Egg remover (http://embrexbiodevices.com/Poultry-BioDevices/Embrex-Egg-Remover/). While this solution prevents the unnecessary opening of eggs, it is still wasteful: all of the eggs with no chick inside are disposed of. That is, the industry incubates more than 12.8 billion eggs annually only to throw them away. Hence, a solution that could determine the fertility status of an egg before incubation would be highly desired. Such a solution would dramatically increase productivity, and save energy, costs, and waste. Also, it would incorporate billions of eggs into the market for human consumption.

There are several patents in the field of identifying fertile eggs. For example, U.S. Pat. No. 5,745,228—Method and apparatus for distinguishing live from infertile poultry eggs uses a light source to determine if the poultry inside the egg is alive. This is the technology used in the Embrex® Egg remover.

U.S. Pat. No. 6,029,080 Method and apparatus for avian pre-hatch sex determination proposes the use of MRI for sexing members of avian species of an egg. While this patent uses MRI technology, it makes no reference to the determination of the fertility status and focuses exclusively on identifying the gonads via MRI for sexing.

U.S. Pat. No. 7,950,439 B1—Avian egg fertility and gender detection suggests the use of an external light source in the form of incandescent, fluorescent or LED lights for the determination of both fertility and gender of an avian egg.

U.S. Pat. No. 6,535,277 B2—Methods and apparatus for non-invasively identifying conditions of eggs via multi-wavelength spectral comparison relies on the use of visible and invisible light at wavelengths between 300 nm and 1,100 nm to identify multiple conditions of an egg, including fertility status.

US2013/0044210 AI—Hyperspectral identification of egg fertility and gender uses light at the mid-IR to determine the fertility of an egg. The inventors of this patent claim that they are capable of determining the fertility status of an egg on day zero (i.e. freshly laid) with an accuracy of 90%.

SUMMARY OF THE INVENTION

The problem underlying a first aspect of the invention is to provide a method and an apparatus for automated non-invasive determining the sex of an embryo of a bird's egg, in particular a chicken egg, which allows for a rapid and reliable determination of the sex of the embryo at an early stage, at which the embryo has not developed a sense of pain yet. This problem is solved by a method according to claim 1, and an apparatus according to claim 25. Preferable embodiments are defined in the dependent claims.

The method according to the first aspect of the invention comprises the steps of conveying a plurality of bird eggs sequentially or in parallel into an NMR apparatus, and subjecting the bird eggs to an NMR measurement, to thereby determine, for each of said eggs, one or more NMR parameters associated with the egg selected from the group consisting of a T1 relaxation time, a T2 relaxation time and a diffusion coefficient.

Herein, each of these "parameters" could correspond to a parameter value representative for a region of interest within the egg, such as the region where or close to where the embryo is located. For example, the "parameter T1" could refer to an average value of T1 values measured in the region of interest.

However, as used herein, the term "parameter" can also refer to a parameter image of a region of said egg, in which parameter values are associated with corresponding pixels or voxels of the image. Note that the term "image" shall not imply that it is something that is necessarily to be visually inspected, but only implies that a parameter value is associated with a given spatial region within the egg, which region is typically referred to in an image as a pixel or voxel. Since in different embodiments of the invention, for each parameter (such as T1, T2 or diffusion coefficient) either a parameter value or a parameter image can be employed, both variants are generally referred to as "parameter" herein for simplicity.

The method further comprises forwarding said one or more NMR parameters, or parameters derived therefrom, to a classification module, said classification module configured for determining, based on said one or more NMR parameters or parameters derived therefrom, a prediction of the sex of the embryo of the associated egg, and conveying said plurality of bird eggs out of said NMR apparatus and sorting the eggs according to the sex prediction provided by said classification module. Herein, the phrase "or parameters derived therefrom" indicates that instead of the parameter value itself, a value derived therefrom can be employed for the classification, for example a normalized value, the square of the value, or the like, which may be more appropriate for the classification purposes.

According to the present invention, the determination of the sex by the classification module is carried out based on one or more specific NMR parameters, namely a T1 relaxation time, a T2 relaxation time and a diffusion coefficient. Surprisingly, it has been found that each of these specific NMR parameters is sensitive to the sex of a chicken embryo.

Accordingly, based on at least one, but typically on a set of more than one of these parameters, the sex of the embryo within the egg can be determined by means of a classification module.

Note that this method is different from the prior art methods based on determining the concentration of estradiol using NMR spectroscopy, or based on determining the sex by analyzing highly resolved NMR images for recognizing sufficiently developed sex organs, which could both be regarded as "deductive" methods, in the sense that certain sex-related features (hormones, sex organs) are expected to be present and then verified using NMR techniques. In contrast to this, the method of the invention is based on parameters only, without necessitating any theory or explanation as to why these parameters are correlated with the sex of the embryo. Instead, the method of the invention is based on the surprising observation that the aforementioned three NMR parameters are characteristic for the sex of the chicken embryo, even at a very early stage. According to the current understanding, the best prediction can be made if the classifying unit receives a set comprising all three of the aforementioned parameters T1, T2 and diffusion coefficient, and bases its prediction thereon, e.g. using a suitable classifier. However, it is not necessary to combine all three of these parameters in one set, instead, it is possible to use only two of these parameters in combination, or one of these parameters in combination with further NMR parameters. In fact, specifically the NMR parameter T1 is sufficiently sex characteristic that a prediction based on this parameter alone is conceivable.

Having the classification module base the decision on parameters only has the advantage that this allows for a very good compromise between high throughput and robust, reliable classification. In general, the measurement and processing of a few individual parameters can be carried out comparatively quickly and easily as e.g. compared to the high resolution imaging that needs to be employed in WO 00/01302, while a robust gender classification can be supported particularly by gender differences in T1, T2 and diffusion coefficient. In fact, various embodiments described below permit determining the gender of each of for example 150 eggs in parallel within less than three minutes, with the potential to decrease this measuring time to two minutes and possibly even to one minute, when optimum use of fast MRI techniques and parallel imaging is made, thereby permitting an average measuring time of one second per egg or below. Moreover, confidence can be increased by increasing the number of parameters in the parameter set, which may amount to an only moderate increase in measuring time and still significantly increase in the prediction quality of the method, even if the interrelation of the parameters and their relation to sex is not or not fully understood. This is fundamentally different when compared to purely deductive methods, where the conclusion about sex is to be reached on certain biological premises (presence of estradiol, absence of testosterone, presence of sex organs in the image). In such deductive methods, the confidence can only be increased by increasing the confidence in the given premises, where a small degree in additional confidence can come at a price of tremendous additional NMR measurement efforts, and consequently reduced yield of the method. Moreover, indications other than the premises remain unconsidered, in particular indications that could be developed at an earlier stage of the embryo than the hormone concentration or the sex organs. For example, according to DE 10 2013 205 426 A1, the concentration of estradiol is preferably determined on the $17^{th}$ day of breeding, where a chicken embryo already senses pain.

In a preferred embodiment, said one or more NMR parameters comprise a set of two or more NMR parameters, of which at least one is selected from said group consisting of a T1 relaxation time, a T2 relaxation time and a diffusion coefficient.

In a preferred embodiment, said set of NMR parameters further comprises one or more of the following parameters: a T2* relaxation time, a T1ρ relaxation time, and a spin density associated with one or more of the nuclei 1H, 13C, 23Na, and 31P, or parameters derived therefrom. While these parameters, according to the current understanding of the inventors, are less characteristic for the sex of the embryo at its early development stage, they can nevertheless be combined with some or all of the three favorite parameters T1, T2 and diffusion coefficient in a set and can be considered by the classifying module, thereby increasing the reliability of the determination.

In addition or alternatively, said set of NMR parameters preferably further comprises one or more of a chemical shift signal of metabolites, in particular water, lipids, amino acids, nucleic acids, or hormones; a chemical shift selective transfer signal; and zero quantum coherence or multiple quantum coherence NMR signals, or parameters derived therefrom. For example, in case of a chemical shift signal spectrum, a "parameter derived therefrom" could be the amplitude of a given peak, the ratio of two peaks, the difference of two peaks or the like. A parameter can be a number, or can be a set of numbers, such as a vector. However, if the classification module is a machine learning module, as explained below, it is also possible to simply provide the full spectrum to the module, which by machine learning is capable of determining the relevant features thereof by itself.

In a preferred embodiment, said classification module is a machine learning module. The inventors have found out that machine learning is a particularly powerful way to determine the sex based on one or more of the aforementioned parameters T1, T2 and diffusion coefficient. Namely, while the available measurements clearly indicate that these parameters are characteristic for the sex of the embryo, there is currently no deductive, biological model available as to exactly why, or by what underlying biological mechanism the sex is related to each of these parameters, or the distribution of the parameters within the egg as represented in a parameter image. Accordingly, machine learning is ideally suitable for recognizing the patterns in any of these parameters, or their combinations that are indicative of the sex of the embryo, allowing for reliable predictions and early prediction dates in the embryo's life. If the classification module is a machine learning module, said NMR parameter values, or parameters derived therefrom, may form feature values presented to the machine learning module as a feature vector. In other words, a parameter value representative for a region of interest within the egg, or a parameter image of a region of the egg may be presented to the machine learning module as a feature vector, or as part of a feature vector.

In a preferred embodiment, the classification module is configured to determine the prediction of the sex of the embryo using a linear classifier. Preferred linear classifiers for the purposes of the present invention are based on one or more of least square linear regression, nearest neighbors, logistic regression, separating hyper planes or perceptrons.

In an alternative preferred embodiment, said classification module is configured to determine the prediction of the sex of the embryo using a nonlinear classifier. Preferred nonlinear classifiers for the purposes of the present invention are based on piecewise polynomials, splines, kernel smoothing, tree-based methods, support vector machines, random forest, boosting, additive and ensemble methods or graph models.

In particularly advantageous embodiments, the classification module is configured to determine the prediction of the sex of the embryo using a deep learning algorithm, which allows for making optimum use of the information regarding sex as expressed in the NMR parameter set. Preferred deep learning algorithms for the purpose of the invention are based on convolutional neural networks, recurrent neural networks or long short-term memory networks.

In alternative embodiments, the classification module may be configured to determine the prediction of the sex of the embryo based on a comparison with parameter values stored in a database.

In a preferred embodiment, the NMR measurement comprises NMR imaging, wherein an NMR imaging plane is arranged such as to intersect the location of the embryo. Herein, the NMR imaging may in particular relate to forming parameter images for one or more of the parameters T1, T2 and diffusion coefficient.

In a preferred embodiment, the eggs are arranged in a regular pattern, in particular in a matrix configuration on a tray during said conveying and NMR measurement.

Preferably, the number of eggs arranged on said tray is at least 36, preferably at least 50 and most preferably at least 120.

In a preferred embodiment, the method is carried out prior to the eighth day of breeding, preferably on the fifth day of breeding, where the embryo has not developed any sense of pain yet.

The problem underlying a second aspect of the invention is to provide a non-invasive technique that is capable of automatically identifying infertile eggs immediately after laying and before incubation, and that is able to handle a large throughput of eggs and does not damage or alter the eggs in any form. This object is achieved by means of a method according to claim 7 and an apparatus according to claim 15. Preferable embodiments are defined in the dependent claims.

The method according to the second aspect of the invention comprises the steps of conveying a plurality of bird eggs sequentially or in parallel into an NMR apparatus, subjecting the bird eggs to an NMR measurement, to thereby determine, for each of said eggs, one or both of
a histogram of diffusion coefficients in various locations in the egg,
an NMR spectrum of the yolk including peaks corresponding to water and fat, determining a prediction of the fertility based on the shape of the histogram of diffusion coefficients and/or on the NMR spectrum, and
conveying said plurality of bird eggs (14) out of said NMR apparatus (18) and sorting the eggs according to the fertility prediction.

The inventors have found that surprisingly, the shape of a histogram of diffusion coefficients in various locations in the egg differs for fertile and infertile eggs. Herein, the histogram indicates how frequent certain diffusion coefficients occur when measurements at various locations in the egg are made. Accordingly, by analyzing the shape of the diffusion coefficient histogram, the fertility can be predicted.

Moreover, the inventors have found that equally surprisingly, the NMR spectra of the yolk of fertile and in infertile eggs differ with regard to their peaks corresponding to water and fat. Accordingly, the shape of an NMR spectrum including such water and fat peaks is likewise characteristic for the fertility and can be employed in the determination.

While only one of the two fertility characteristics may be used in the method, in preferred embodiments, both characteristics are combined in the determination, to thereby increase the reliability of the prediction.

Since the eggs can be subjected to NMR measurements without causing any harm or damage to the shell or interior, the hatching rate is not adversely affected by this measurement. At the same time, unnecessary incubation of infertile eggs can be avoided. Moreover, since the infertility is determined prior to incubation, those eggs found to be infertile can still be used for eating, which is not possible once incubation has started.

While there are of course many ways to analyze the shape of a diffusion coefficient histogram, in a preferred embodiment, determining the fertility based on the shape of the histogram of diffusion coefficients comprises comparing the frequency of occurrence of at least two different diffusion coefficients or diffusion coefficient ranges. This is a particularly simple way to characterize the shape of the diffusion coefficient histogram, which has proven to give surprisingly reliable results.

In a preferred embodiment, said at least two different diffusion coefficients, or the centers of said at least two diffusion coefficient ranges are separated by between 0.5 and 2.5 mm$^2$/s, preferably by between 0.75 and 1.5 mm$^2$/s.

Of said at least two different diffusion coefficients, or of the centers of said at least two diffusion coefficient ranges, preferably one is located in a range of 0.6 to 1.3 mm$^2$/s, preferably in a range of 0.7 to 1.2 mm$^2$/s, and the other one is located in a range of 1.5 to 2.5 mm$^2$/s, preferably in a range of 1.7 to 2.3 mm$^2$/s.

In a preferred embodiment, said various locations in the egg are evenly distributed in the egg, and in particular, correspond to voxels of a diffusion coefficient image.

Having regard to the spectrum, the inventors have observed that when the spectrum is e.g. normalized to the peaks corresponding to fat, the peak corresponding to water is larger in an infertile egg as compared to a fertile egg. Accordingly, one way to determine the fertility is via the ratio of the water and fat peaks. However, there are different ways of classifying fertility based on the NMR spectra. In particular, it is possible to present the spectrum, or certain characteristics of the spectrum, such as peak heights and peak locations to a machine learning module which carries out the classification.

In either of the methods according to the first or the second aspect of the invention, the eggs are arranged in a regular pattern, in particular in a matrix configuration on a tray during said conveying and NMR measurement. Preferably, the number of eggs arranged on said tray is at least 36, preferably at least 50 and most preferably at least 120.

The invention further relates to an apparatus for automated noninvasive determining the sex of an embryo of a bird's egg, comprising: an NMR apparatus and a conveying device for conveying a plurality of bird eggs sequentially or in parallel into and out of said NMR apparatus. The NMR apparatus is configured for subjecting the bird eggs to an NMR measurement, to thereby determine, for each of said eggs, one or more NMR parameters associated with the egg selected from the group consisting of a T1 relaxation time, a T2 relaxation time and a diffusion coefficient, wherein each of said parameters corresponds to
a parameter value representative for a region of interest within the egg, or a parameter image of a region of said egg, in which parameter values are associated with corresponding pixel or voxel of the image.

The apparatus further comprises a classification module configured to receive said one or more NMR parameters, or parameters derived therefrom, said classification module configured for determining, based on said one or more NMR parameters or parameters derived therefrom, a prediction of the sex of the embryo of the associated egg. Finally, the apparatus comprises an egg sorting device for sorting the eggs according to the sex prediction provided by said classification module.

In a preferred embodiment, said one or more NMR parameters comprise a set of two or more NMR parameters, of which at least one is selected from said group consisting of a T1 relaxation time, a T2 relaxation time and a diffusion coefficient.

Preferably, said set of NMR parameters further comprises one or more of the following parameters: a T2* relaxation time, a T1ρ relaxation time, and a spin density associated with one or more of the nuclei 1H, 13C, 23Na, and 31P.

In addition or alternatively, said set of NMR parameters preferably further comprises one or more of a chemical shift signal of metabolites, in particular water, lipids, amino acids, nucleic acids, or hormones; a chemical shift selective transfer signal; and zero quantum coherence or multiple quantum coherence NMR signals.

In a preferred embodiment, said classification module is a machine learning module.

Preferably, said NMR parameter values, or parameters derived therefrom, form feature values presented to the machine learning module as a feature vector.

In a preferred embodiment, said classification module is configured to determine the prediction of the sex of the embryo using a linear classifier, in particular a linear classifier based on one or more of least square linear regression, nearest neighbors, logistic regression, separating hyper planes or perceptrons.

In an alternative preferred embodiment, said classification module is configured to determine the prediction of the sex of the embryo using a nonlinear classifier, in particular a nonlinear classifier based on piecewise polynomials, splines, kernel smoothing, tree-based methods, support vector machines, random forest, boosting, additive and ensemble methods or graph models.

In yet an alternative preferred embodiment, said classification module (38) is configured to determine the prediction of the sex of the embryo using a deep learning algorithm, in particular a deep learning algorithm based on convolutional neural networks, recurrent neural networks or long short-term memory networks.

In an alternative embodiment, the classification module (38) is configured to determine the prediction of the sex of the embryo based on a comparison with parameter values stored in a database.

The invention further relates to apparatus for automated noninvasive determining the fertility of a bird's egg, comprising an NMR apparatus and a conveying device for conveying a plurality of bird eggs sequentially or in parallel into and out of said NMR apparatus, wherein said NMR apparatus is configured for subjecting the bird eggs to an NMR measurement, to thereby determine, for each of said eggs one or both of a histogram of diffusion coefficients in various locations in the egg, an NMR spectrum of the yolk including peaks corresponding to water and fat, wherein said apparatus is further configured for determining a prediction of the fertility based on the shape of the histogram of diffusion coefficients and/or on the NMR spectrum, wherein said apparatus further comprises an egg sorting device for sorting the eggs according to the fertility prediction.

In a preferred embodiment, said determining of the fertility based on the shape of the histogram of diffusion coefficients by the apparatus comprises comparing the frequency of occurrence of at least two different diffusion coefficients or diffusion coefficient ranges.

In a preferred embodiment, said at least two different diffusion coefficients, or the centers of said at least two diffusion coefficient ranges are separated by between 0.5 and 2.5 mm$^2$/s, preferably by between 0.75 and 1.5 mm$^2$/s.

In a preferred embodiment, of said at least two different diffusion coefficients, or the centers of said at least two diffusion coefficient ranges, one is located in a range of 0.6 to 1.3 mm$^2$/s, preferably in a range of 0.7 to 1.2 mm$^2$/s, and the other one is located in a range of 1.5 to 2.5 mm$^2$/s, preferably in a range of 1.7 to 2.3 mm$^2$/s.

In a preferred embodiment, said various locations in the egg are evenly distributed in the egg, and in particular, correspond to voxels of a diffusion coefficient image.

In a preferred embodiment, said apparatus is configured to determine a prediction of fertility based on the NMR spectrum based on the ratio of peaks corresponding to water and fat in said NMR spectrum.

Irrespective of whether the apparatus is configured for determining the sex of the embryo or the fertility of the egg, in preferred embodiments, the apparatus further comprises a tray on which said eggs can be arranged in a regular pattern, in particular in a matrix configuration, during said conveying and NMR measurement.

In a preferred embodiment, the number of eggs that can be arranged on said tray is at least 36, preferably at least 50 and most preferably at least 120.

In a preferred embodiment, said NMR apparatus comprises an array of RF coils for applying RF magnetic fields to the eggs located on the tray and/or for detecting NMR signals, said array of RF coils comprising one or more of a plurality of coils arranged in a plane located above the tray loaded with eggs when conveyed to the NMR apparatus, a plurality of coils arranged in a plane located underneath the tray loaded with eggs when conveyed to the NMR apparatus, a plurality of coils arranged in vertical planes extending between rows of eggs on the tray when conveyed to the NMR apparatus, which rows extend in parallel with the conveying direction of the tray into and out of the NMR apparatus.

In case of the plurality of coils arranged in a plane located above or underneath the tray loaded with eggs, the ratio of the number of coils to the number of eggs arranged on said tray is between 1:1 to 1:25, preferably between 1:1 to 1:16, and most preferably between 1:1 to 1:5.

In a preferred embodiment, said NMR apparatus comprises an array of RF coils for applying RF magnetic fields to the eggs located on the tray (16) and/or for detecting NMR signals, said array of RF coils being integrated with or attached to said tray.

Herein, the tray preferably comprises a plurality of dimples or pockets for receiving a corresponding egg, wherein a number of coils is associated with each of said dimples or pockets, wherein said number of coils per dimple or pocket is at least 2, preferably at least 3, and most preferably at least 4, and/or wherein at least some of said coils are arranged vertically with respect to the main plane of the tray, or with an angle of at least 5°, preferably of at least 75° and most preferably of at least 80° with respect to the main plane of the tray.

SHORT DESCRIPTION OF THE FIGURES

Figure 3:
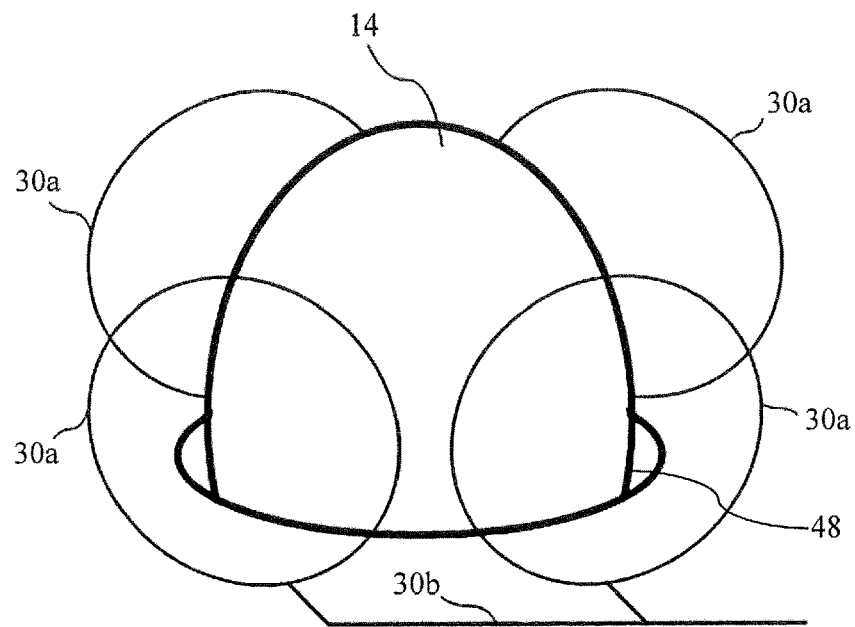

FIG. 3 schematically shows a portion of a tray including a dimple for receiving an egg and four RF coils integrated with the tray surrounding the egg.

Figure 4:
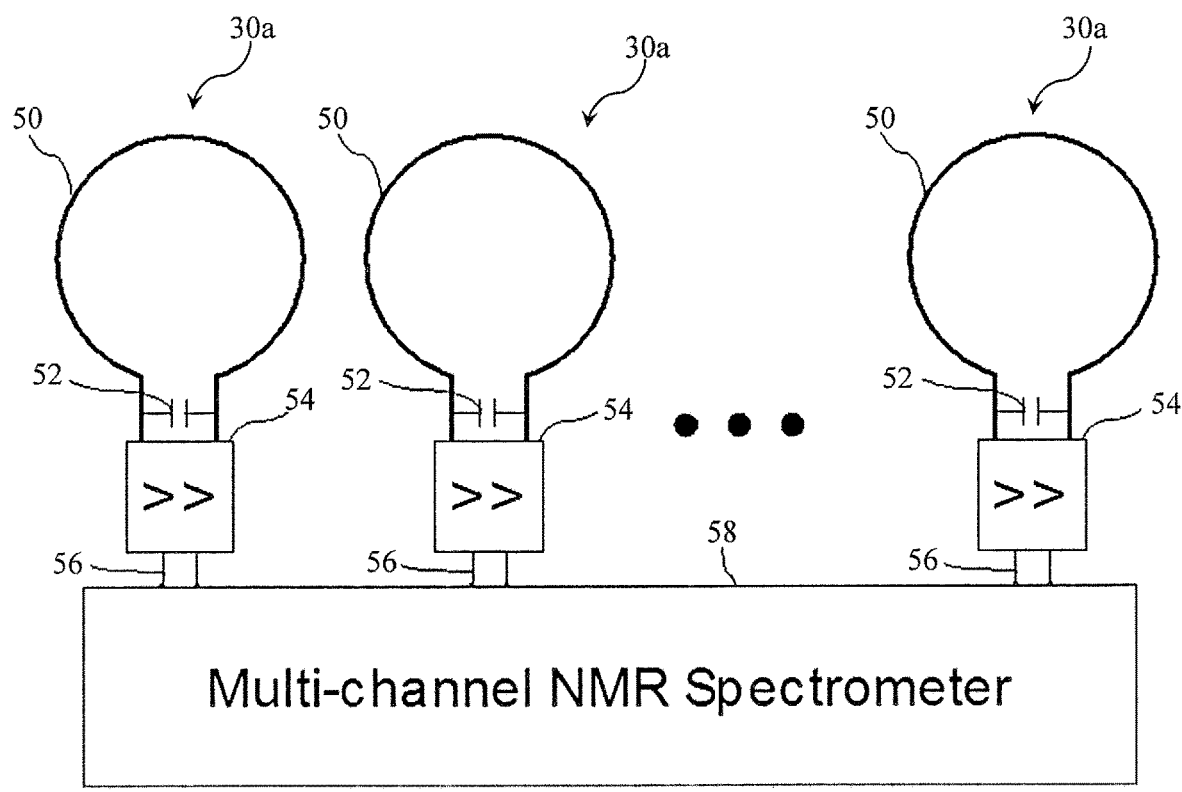

FIG. 4 shows further details of the coil arrays of FIGS. 2A to C and 3.

Figure 1:
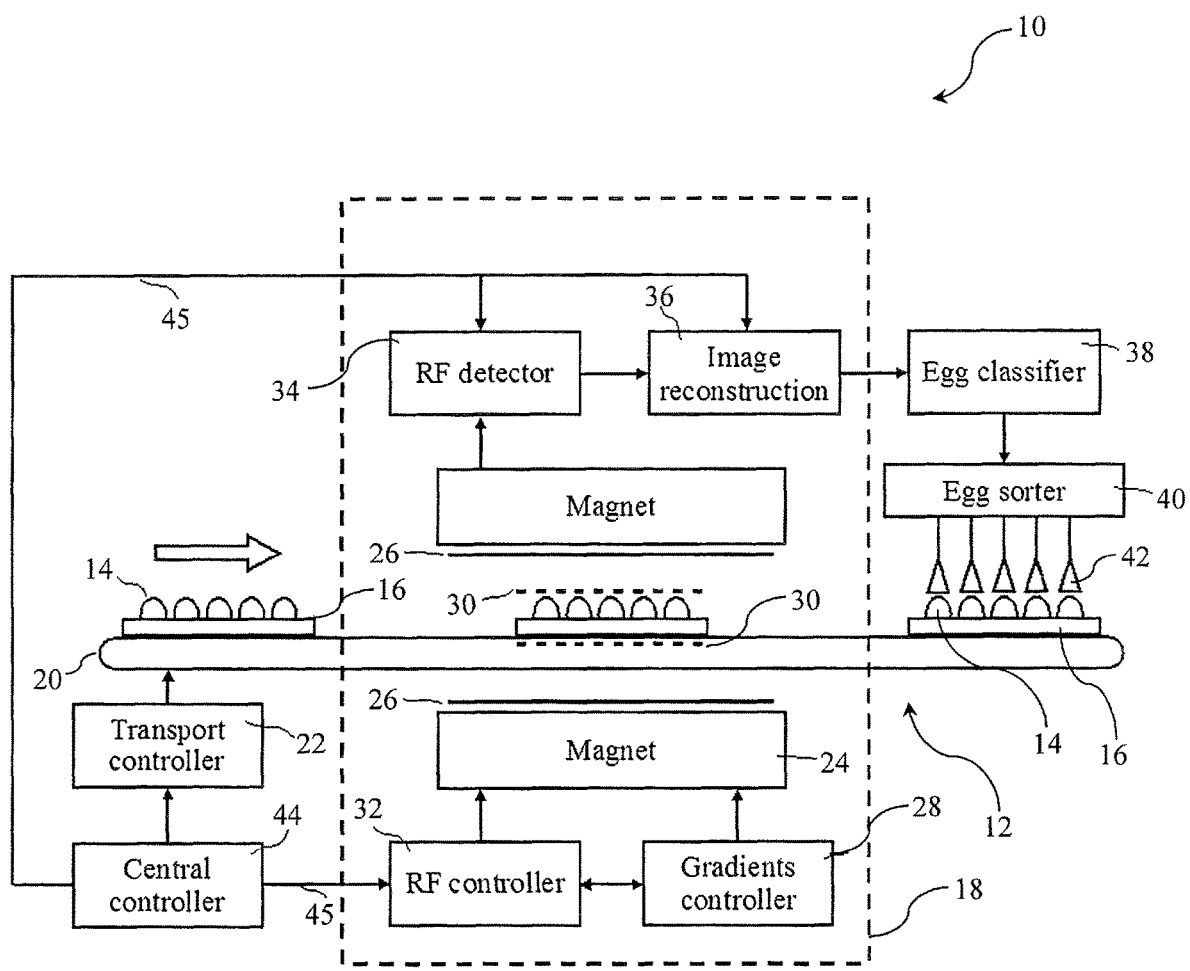
FIG. 1 is a schematic illustration of an apparatus for automated noninvasive determining the sex of an embryo of a bird's egg or the fertility of a bird's egg.
Figure 5:
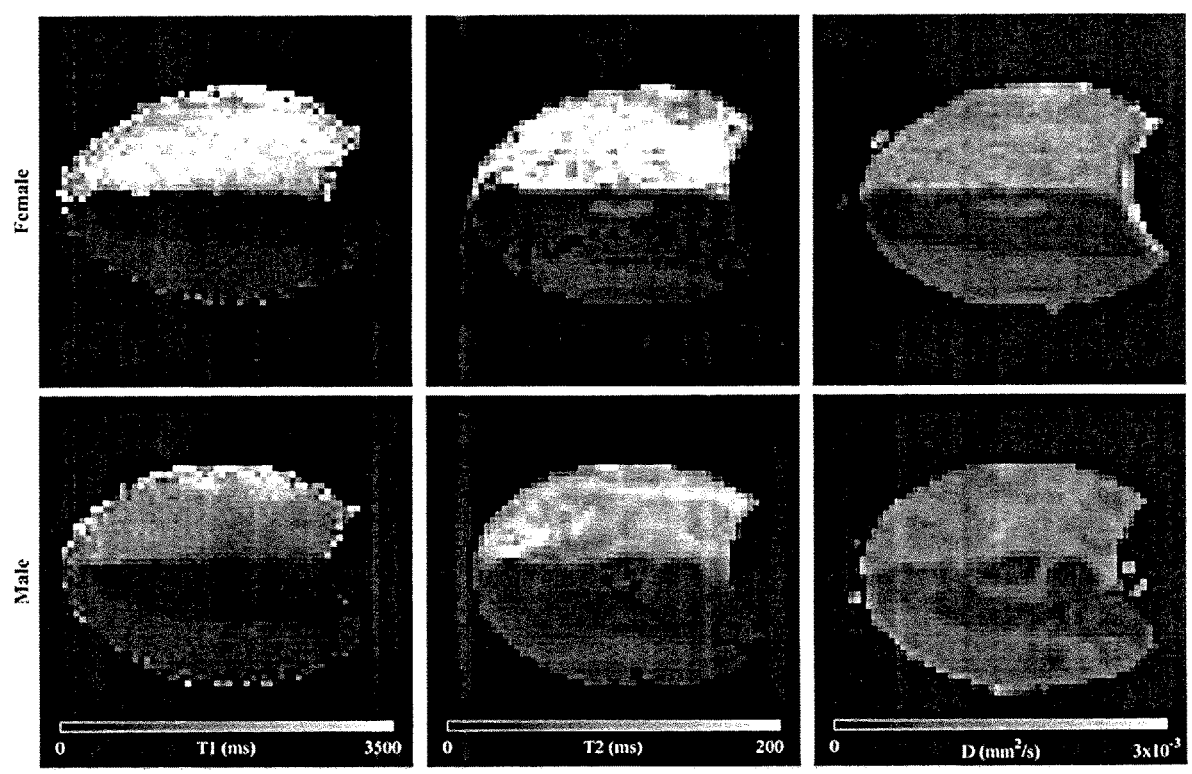

FIG. 5 shows six NMR parameter images taken by the NMR apparatus of FIG. 1

Figure 6:
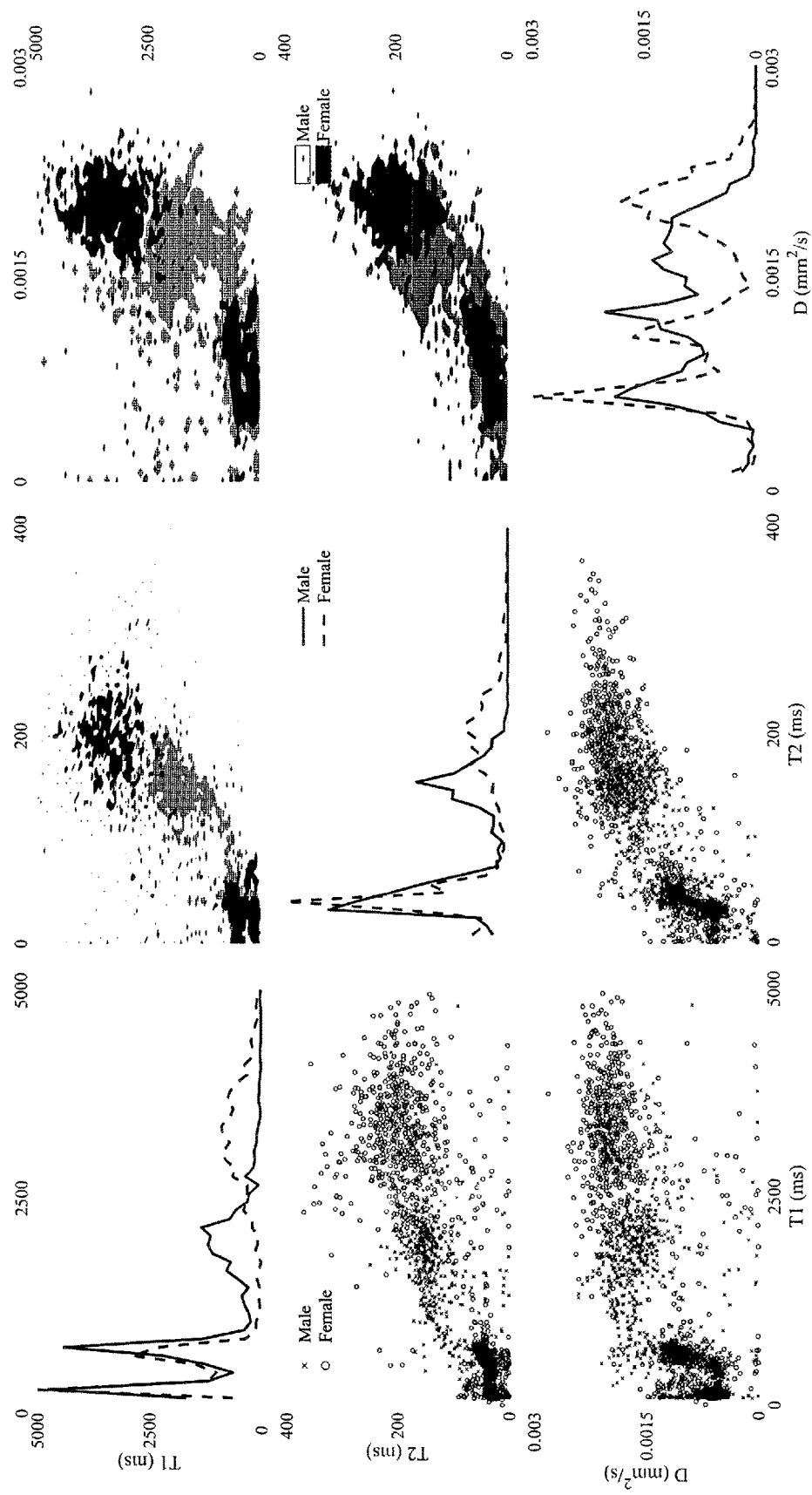

FIG. 6 shows pairwise combinations of parameters T1, T2 and D in the off-diagonal diagrams and histograms for each of the parameters T1, T2 and D in the diagrams arranged along the diagonal.

Figure 7:
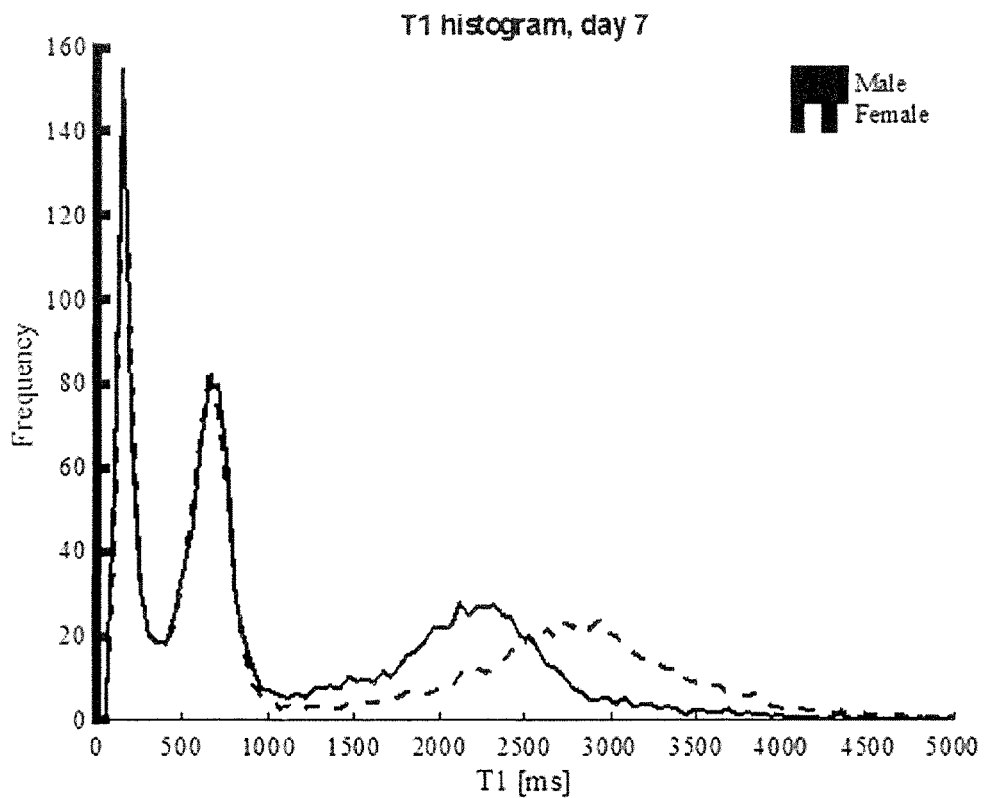

FIG. 7 shows an averaged histogram for T1 values for male and female embryos.

Figure 8:
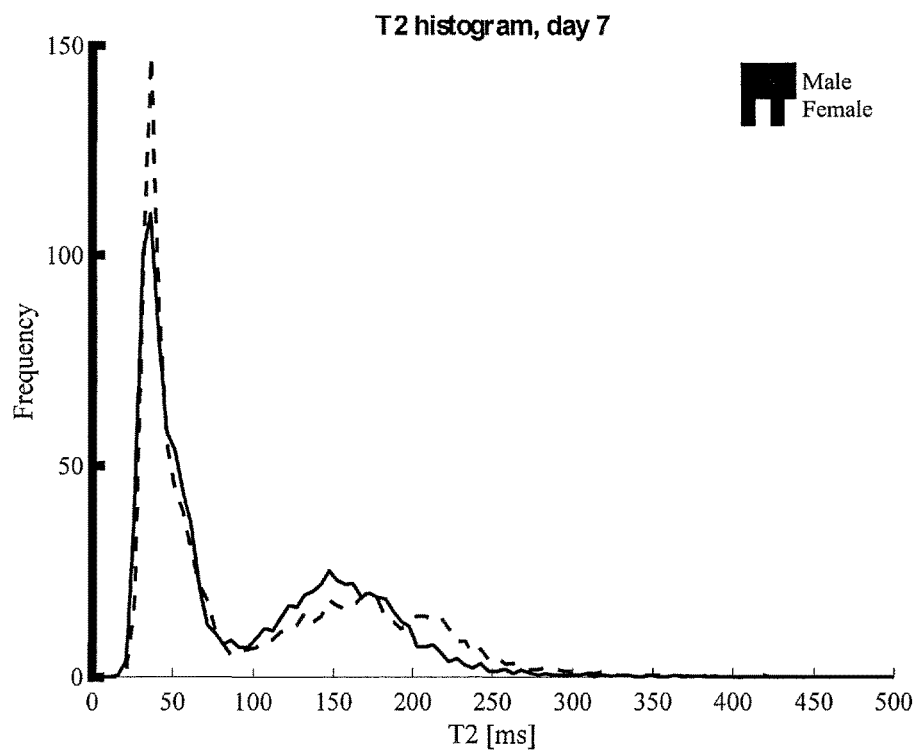

FIG. 8 shows an averaged histogram for T2 values for male and female embryos.

Figure 9:
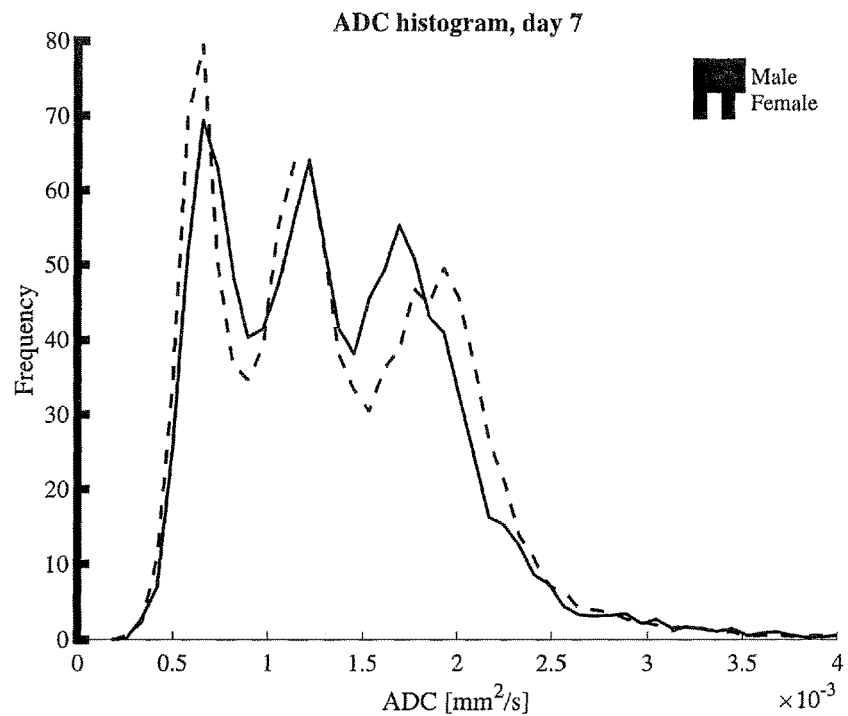

FIG. 9 shows an averaged histogram for diffusion coefficients for male and female embryos.

Figure 10:
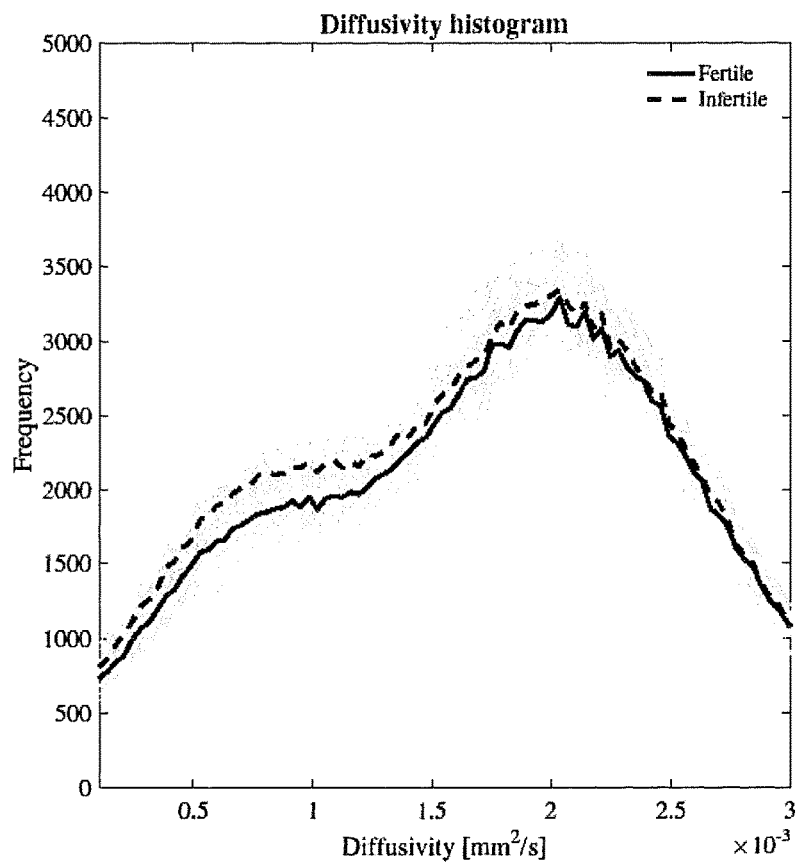

FIG. 10 shows an averaged histogram of the diffusion coefficient observed for a plurality of fertile eggs (solid line) and infertile eggs (broken line).

Figure 11:
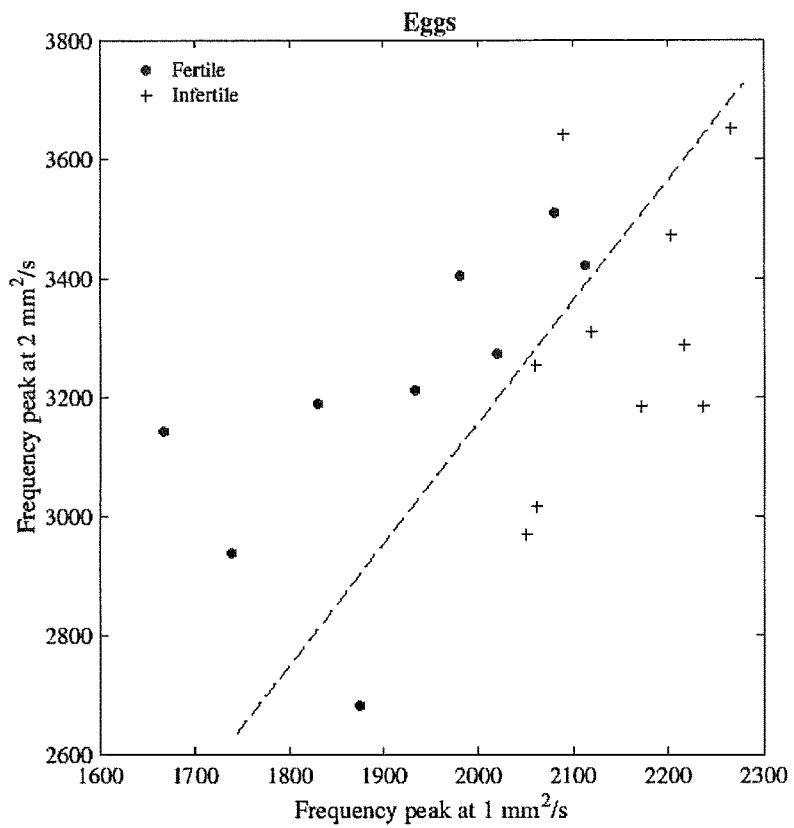

FIG. 11 is a scatterplot showing pairs of diffusion coefficient histogram values at 1 mm/s and 2 mm/s for a plurality of eggs.

Figure 12:
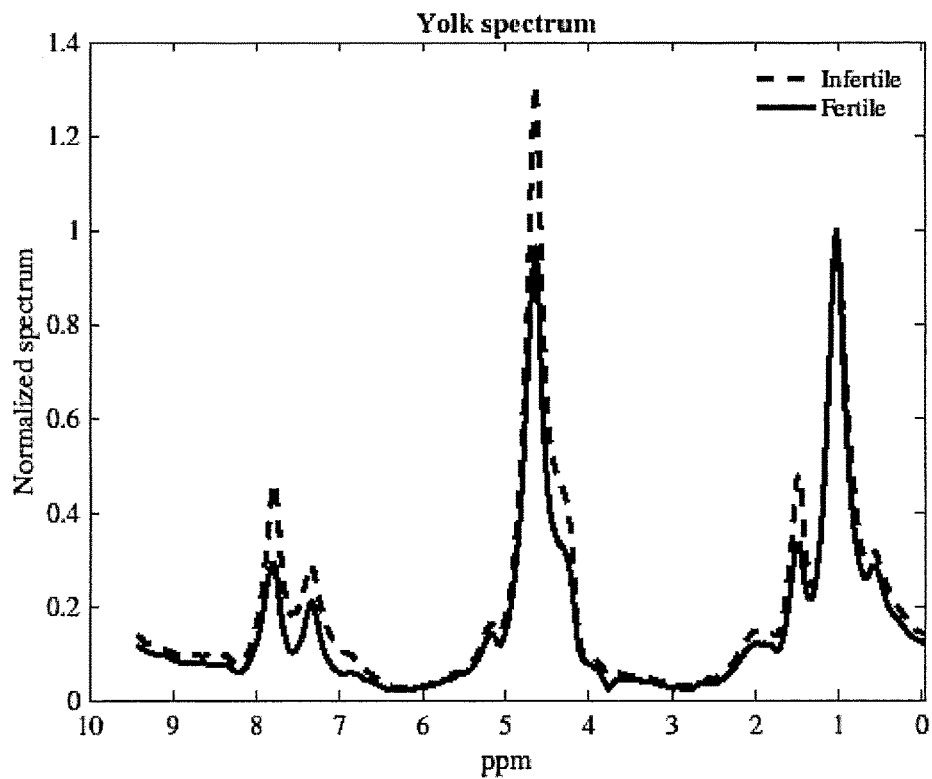

FIG. 12 shows NMR spectra for fertile and infertile eggs.

Figure 13:
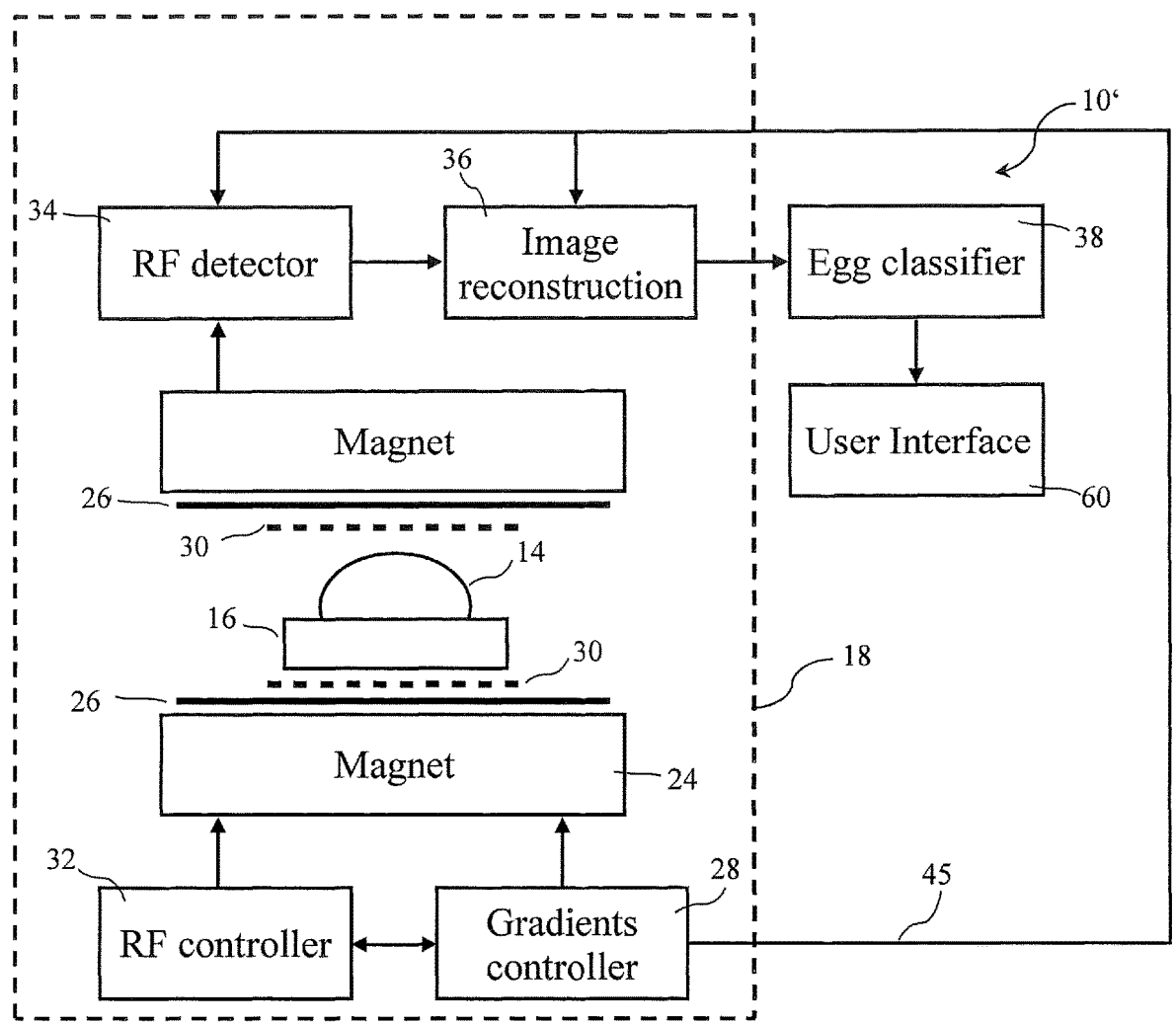

FIG. 13 is a schematic illustration of a simplified apparatus for non-automated noninvasive determining the sex of an embryo of a bird's egg or the fertility of a bird's egg.

Figure 14:
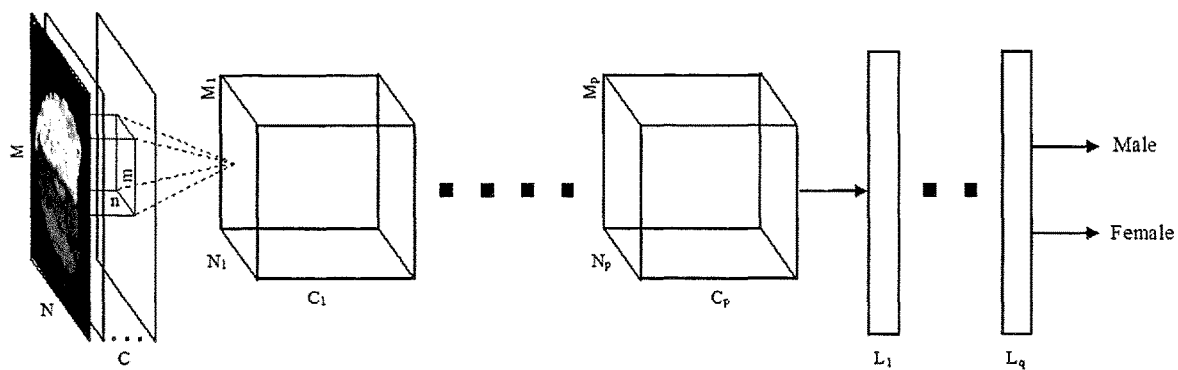

FIG. 14 is a schematic illustration of an architecture of a machine learning classifier for egg sex determination based on convolutional neural networks.

DESCRIPTION OF THE PREFERRED EMBODIMENT

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to one skilled in the art to which the invention relates.

FIG. 1 shows a schematic representation of an apparatus to according to a preferred embodiment of the invention. The apparatus 10 comprises a conveying device 12 for conveying a plurality of eggs 14 arranged in a matrix configuration on a tray 16 into and out of an NMR apparatus 18, which is represented by the hatched box in the figure. In the embodiment shown, the conveying device 12 comprises a conveyor belt 20 on which the trays 16 may be carried. The movement of the conveyor belt 20 is controlled by a corresponding transport controller 22.

The NMR apparatus 18 comprises a magnet arrangement 24 for providing an external magnetic field in z-direction with which the nuclear spins may interact. The z-direction of the magnetic field coincides with the transport direction on the conveyor belt 20, but this is not crucial for the function of the apparatus to. In the embodiment shown, the magnet arrangement 22 generates a static magnetic field having a field strength of 1 T, but the invention is not limited to this. Instead, a wide variety of magnetic field strengths may be used, and in alternative embodiments of the invention, even the earth magnetic field strength could be sufficient, as is demonstrated in Stepišnik, J., Eržen, V. & Kos, M. *NMR imaging in the earth's magnetic field. Magn. Reson. Med.* 15, 386-391 (1990), and Robinson, J. N. et al. *Two-dimensional NMR spectroscopy in Earth's magnetic field. J. Magn. Reson.* 182, 343-347 (2006).

Further, the NMR apparatus 18 comprises gradient coils 26 which are used to generate spatial gradient fields that are used for image encoding, or in other words, space resolved NMR measurements, in a manner per se known to the skilled person, and further described in Lauterbur, P. C. *Image formation by induced local interactions. Examples employing nuclear magnetic resonance. Nature* 242, 190-191 (1973). In addition, the gradient coils 26 are also used to increase the local homogeneity of the external magnetic field created by the magnet arrangement 24. The gradient fields applied by the gradient coils 26 are controlled by a gradient controller 28. In the embodiment shown, the gradient controller 28 is optimized for an efficient coverage of the measurement space (the k-space), in order to increase the measurement speed. In particular, the gradient controller 28 is preferably configured for carrying out echo-planar-imaging. For details of echo-planar-imaging, reference is made to Stehling, M., Turner, R. & Mansfield, P. *Echo-planar imaging: magnetic resonance imaging in a fraction of a second. Science* (80-.). 254, 43-50 (1991), and Mansfield, P. & Maudsley, A. A. *Planar spin imaging by NMR. J. Phys. C Solid State Phys.* 9, L409-L412 (1976). In the alternative, the gradient controller controller 28 can control the gradient coils 26 to carry out spiral readouts with time-optimal gradient design, as described in Hargreaves, B. A., Nishimura, D. G. & Conolly, S. M. *Time-optimal multidimensional gradient waveform design for rapid imaging. Magn. Reson. Med.* 51, 81-92 (2004), which allows for very rapid NMR imaging.

Multiple RF coils 30 are arranged such as to surround the tray 16 loaded with eggs 14 on the conveyor belt 20 when the tray 16 is conveyed to the NMR apparatus 18. As the skilled person will appreciate, the RF coils 30 are used for providing RF pulses that excite spins, and in particular, the spins of hydrogen atoms inside the eggs 14. The timing, shape and strength of the pulses are controlled by the RF controller 32. A serial manipulation of the RF pulses and gradients allows for modulation of the measured signal for fast image encoding. In order to allow for high throughput measurements, fast pulse sequences, such as fast-low angle shot imaging or quantitative transient imaging may be deployed, as described in more detail in the the articles Haase, A., Frahm, J., Matthaei, D., Hanicke, W. & Merboldt, K. D. *FLASH imaging. Rapid NMR imaging using low*

*flip-angle pulses. J. Magn. Reson.* 67, 258-266 (1986)) and Gómez, P. A. et al. *Accelerated parameter mapping with compressed sensing: an alternative to MR Fingerprinting. Proc Intl Soc Mag Reson Med* (2017), co-authored by the present inventors and included herein by reference. These fast pulse sequences are designed to be sensitive to different relevant parameters employed in the present invention, in particular T1 and T2 relaxation and diffusion, but also to fat-water content or magnetization transfer.

Moreover, the precession movement of the excited spins in the external magnetic field provided by the magnet arrangement 24 lead to current flux in the RF coils 30 that can be detected by an RF detector 34. The RF detector 34 translates the current flux from the RF coils 30 into an interpretable signal. This includes analog to digital conversion, signal demodulation and amplification.

The NMR apparatus 18 further comprises an image reconstruction module 36. In preferred embodiments, the measurements from different RF coils 30 will be combined using parallel imaging techniques, and an image reconstruction is achieved through the application of fast Fourier transform (FFT) on the acquired measurements. For details of parallel imaging techniques, reference is made to Pruessmann, K. P., Weiger, M., Scheidegger, M. B. & Boesiger, P. *SENSE: sensitivity encoding for fast MRI. Magn. Reson. Med.* 42, 952-962 (1999), and Uecker, M. et al. *ESPIRiT—An eigenvalue approach to autocalibrating parallel MRI: Where SENSE meets GRAPPA. Magn. Reson. Med.* 71, 990-1001 (2014).

When non-Cartesian sampling is employed, the nonuniform FFT as described in Fessler, J. A. and Sutton, B. *Nonuniform Fast Fourier Transforms Using Min Max Interpolation. IEEE Trans. Signal Process.* 51, 560-574 (2003) may be employed. In the embodiment shown, the image reconstruction module 36 implements advanced reconstruction algorithms, such as low-rank matrix recovery or iterative algorithms. The image reconstruction module 36 is configured to process data of different dimensionality, namely 1D or 2D NMR signals, 2D images, 3D volumes, and 4D time series.

The data processed by the image reconstruction module 36 are transmitted to an egg classification module 38. In the embodiment shown, the egg classification module 38 has two purposes, segmentation and classification. In the high throughput device, the egg classification module 38 first segments the incoming images into image portions corresponding to individual eggs 14. Thereafter, the image portion corresponding to each individual egg 14 is classified according to its sex in a manner to be described in more detail below.

The result of the egg classification is provided to an egg sorting device 40. In the embodiment shown, the classification result is provided to the egg sorting device 40 in the form of a matrix containing the encoded sexes of the eggs 14 on a given tray 16. Based on this information, the egg sorting device 40 may sort out eggs 14 determined as including male embryos, or may rearrange the eggs 14 on the tray 16 according to sex. As schematically shown in FIG. 1, the egg sorter 40 has as many cups 42 as there are eggs 14 on the tray 16, wherein said cups 42 are connected to a vacuum device (not shown). When a cup 42 is moved closely to the corresponding egg 14, the egg 14 will be attracted to and fixed to the cup 42 by vacuum suction, such that it can be safely picked up and gently be put down at a different location.

Finally, a central controller 44 is provided, which is connected for data communication with each of the afore- mentioned components involved in the NMR measurement, image reconstruction egg classification and egg sorting process, via corresponding data channels 45.

The NMR apparatus 18 which is devised for egg classification in industrial environment addresses a well-defined scanning geometry. Eggs 14 are introduced into the NMR apparatus 18 arranged in a matrix configuration with M rows and N columns on a corresponding tray 16, where the columns are arranged parallel to the conveying direction on the conveyor belt 20 of FIG. 1. Various embodiments of the invention employ an array 30 of RF coils 30a that is designed to maximize signal-to-noise ratio and minimize acquisition time, which will be described next with reference to FIGS. 2 to 4. Since the signal amplitude of radiofrequency decays with the square of the distance from the emitting source, the preferred designs aim at placing the RF coils 30a as closely as possible to the eggs 14. Moreover, having an array 30 of coils 30a creates spatial redundancy in the receiving field that can be exploited to reduce the scan time.

Figure 2A:
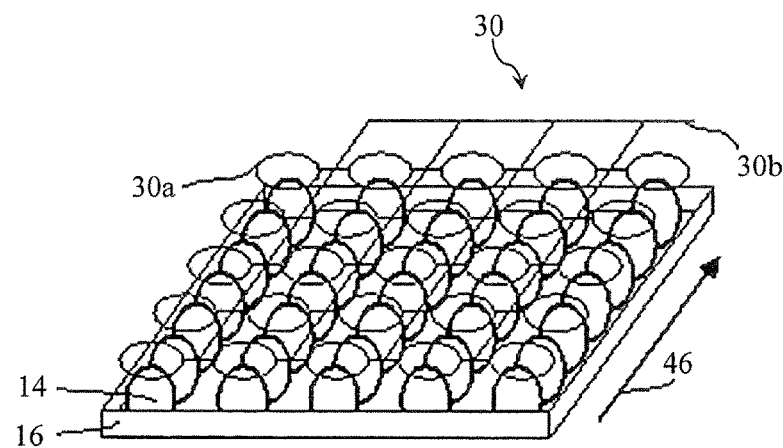
FIG. 2A is a perspective view of an RF coil array arranged in a plane parallel to and slightly above a tray loaded with eggs.
Figure 2B:
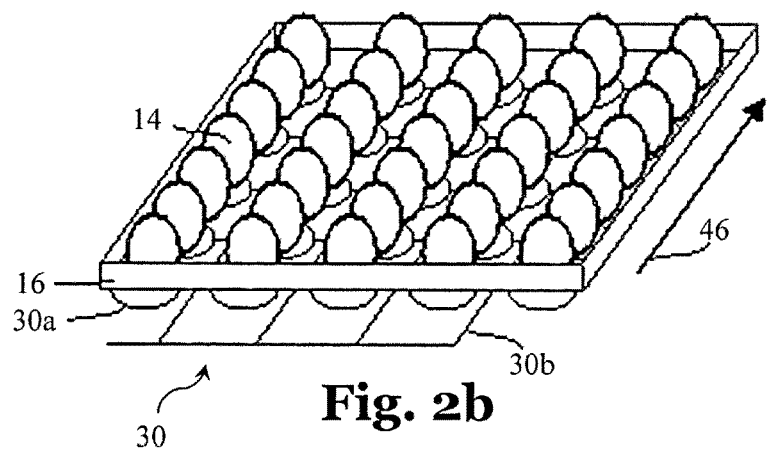
FIG. 2B is a perspective view of an RF coil array arranged in a plane parallel to and slightly below a tray loaded with eggs.
Figure 2C:
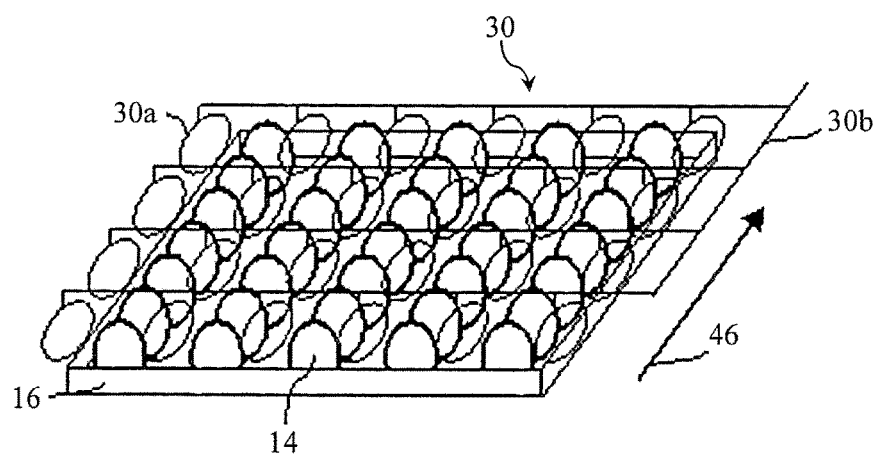
FIG. 2C is a perspective view of an RF coil array in which coils are arranged in vertical planes extending between rows of eggs on the tray, which rows extend in parallel with the conveying direction of the tray.

FIGS. 2A to 2C show three different RF coil arrays 30 which are particularly suitable for establishing preferable signal-to-noise ratios and minimum acquisition times. In each of FIGS. 2A to 2C, an array 30 of RF coils 30a is schematically shown together with the tray 16 loaded with eggs 14. Each individual RF coil 30a of the RF coil array 30 is shown to have a loop geometry for simplicity, but different geometries may likewise be implemented. In the embodiment of FIG. 2A, the individual RF coils 30a are arranged in a plane parallel to and slightly above the tray 16. The number of individual RF coils 30a may, but need not correspond to the number of eggs 14. Preferably, the ratio of the number of RF coils 30a to the number of eggs 14 arranged on the tray 16 is between 1:1 to 1:25, preferably between 1:1 to 1:16, and most preferably between 1:1 to 1:5. Each of the individual RF coils 30a is connected via a corresponding transmission line Sob with the RF controller 32 and with the RF detector 34. While in the simplified figures all of the transmission lines 30b are shown as a single cable, it is to be understood that this cable includes a plurality of individual leads such that each RF coil 30a of the RF coil array 30 can be individually controlled by the RF controller 32 and read out by the RF detector 34. The arrow 46 denotes the direction of the conveying direction of the tray 16 by the conveying device 12.

FIG. 2B shows a similar RF coil array 30 as that of FIG. 2A, which is however placed underneath the tray 16.

FIG. 2C shows an RF coil array 30 of RF coils 30a which are arranged vertically and placed to the side of the eggs 14, rather than above or below, as is the case in FIGS. 2A and 2B. In order not to interfere with the eggs 14 moving on the conveyor belt 20, the RF coils 30a of the RF coil array 30 are arranged in vertical planes extending between the rows of eggs 14 on the tray 16, which rows extend in parallel with the conveying direction of the tray 16 by the conveying device 12 as indicated by the arrow 46.

Since the embryo will always float to the top of the egg 14, the area of interest is mainly located in the upper half thereof. This implies that the configurations of FIG. 2A (superior RF coil array 30 plane) and FIG. 2C (RF coils 30a arranged in longitudinal, vertical planes) allow for smaller distances between the RF coils 30a of the RF coil array 30 and the regions of interest in the eggs 14 than the configuration of FIG. 2B, and hence for a favorable signal-to-noise ratio. However, in various embodiments, the RF coil array 30 arranged in a plane below the tray 16 as shown in FIG. 2B could be used instead of, or in combination with any of the configurations of FIGS. 2A and 2C. In fact, any two, or all three of the configurations of FIGS. 2A, 2B and 2C can be combined in the NMR apparatus 18.

In an alternative embodiment, the RF coils 30a are attached to or integrated in the tray 16, as shown in FIG. 3. FIG. 3 schematically shows a portion of the tray 16, in which a dimple 48 for receiving an egg 14 is formed. Attached to or integrated with the tray 16 are four RF coils 30a surrounding the egg 14. Generally, one or more RF coils 30a per dimple 48 may be provided. Other particularly favorable embodiments provide for three, five, six or eight RF coils 30a per dimple 48. Attaching to or integrating the RF coils 30a with the tray 16 allows for a denser integration of RF coils 30a and smaller distances with the corresponding eggs 14, without interfering with the conveying of the eggs 14 on the tray 16, which allows for particularly high signal-to-noise ratios and minimized acquisition time. However, in this embodiment, the eggs 14 need to be transferred from transportation trays (not shown) to specific NMR trays 16, and later on to the incubation trays (not shown).

FIG. 4 shows further details of the RF coil arrays 30, which may apply irrespective of the particular geometrical arrangement of the RF coils 30a in the RF coil array 30, and may hence apply for any of the embodiments shown in FIGS. 2A, 2B, 2C and 3. As is schematically shown in FIG. 4, each of the RF coils 30a may comprise an antenna section 50, which in the shown embodiments has the shape of a circular loop. However, antenna sections 50 with different geometries, such as Helmholtz coils, solenoidal coils, saddle coils, or birdcage coils may likewise be employed.

Further, each RF coil 30a comprises a tuning capacitor 52 for reducing the mutual inductance and to tune the center frequency, and a pre-amplifier 54 which improves the tuning, matching and to decoupling. Moreover, each RF coil 30a is connected via transmission lines 56 with a multi-channel NMR spectrometer 58, which combines the functionalities of the RF controller 32 and the RF detector 34 shown in FIG. 1.

Obviously, the NMR measurement time is critical for a high throughput device. Preferred embodiments of the invention are therefore optimized for high-speed acquisition and reconstruction. In particular, the RF coil arrays 30 described above are suitable for parallel imaging, to thereby acquire less information per RF coil 30a and combining it using spatial redundancy, such as to speed up the measurement.

Preferred embodiments of the invention employ the so-called SENSE method described in Pruessmann, K. P., Weiger, M., Scheidegger, M. B. & Boesiger, P. *SENSE: sensitivity encoding for fast MRI. Magn. Reson. Med.* 42, 952-962 (1999), which makes use of the spatial redundancy to acquire a subsample of the k-space and reconstruct non-aliased images. A related method that is likewise applicable is the so-called Generalized Auto calibrating Partially Parallel Acquisition (GRAPPA) method, as described in Griswold, M. A. et al, *Generalized auto calibrating partially parallel acquisitions (GRAPPA), Magn. Res. Med* 47, 1202-1210 (2002).

To further increase the throughput, multiband technologies are employed which use several excitation frequencies to allow parallel acquisition at different spatial locations along the bore of the magnet arrangement 42, thereby also reducing the total scan time. A more detailed explanation of the multiband technology is given in Feinberg, D. A. et al. *Multiplexed echo planar imaging for sub-second whole brain fmri and fast diffusion imaging. PLoS One* 5, (2010), which is included herein by reference.

On top of these techniques, in preferred embodiments a so-called compressed sensing is employed, which reduces the number of measuring points necessary to reconstruct an image, thereby introducing a new acceleration factor. A determination of compressed sensing is given in Lustig, M., Donoho, D. & Pauly, J. M. *Sparse MRI: The application of compressed sensing for rapid MR imaging. Magn. Reson. Med.* 58, 1182-1195 (2007).

Moreover, in preferred embodiments, the imaging is carried out in the transient state, which can be carried out in an ultrafast manner and use quantitative parameters, as is described in the works co-authored by the present inventors, see Gómez, P. A. et al. *Accelerated parameter mapping with compressed sensing: an alternative to MR Fingerprinting. Proc Intl Soc Mag Reson Med* (2017). Another suitable way of transient imaging is described in Ma, D. et al. *Magnetic resonance fingerprinting. Nature* 495, 187-192 (2013).

The RF coil array configurations and the image reconstruction methods previously introduced allow for quickly imaging the 3D space that contains the N×M array of eggs 14. Depending on the RF coil geometry and on the processing method chosen, in some embodiments one image per egg 14 will be reconstructed, while in other embodiments, a single image per tray 16 will be reconstructed. In the case of a single image per egg 14, each image can be classified individually. In the case of one image per tray 16, the individual eggs 14 in the image need first to be segmented prior to classification. There are multiple segmentation techniques that can be employed; but, given the simplicity of geometry of the trays 16, the preferred solution is to pre-define a grid corresponding to each dimple 48 with a single egg 14.

FIG. 5 shows six NMR parameter images taken by the NMR apparatus 18 of FIG. 1. The upper row of images corresponds to an egg including a female seven-day-old embryo, while the lower row of images corresponds to an egg including a male seven-day-old embryo. As was explained in the introductory part of the application, a "parameter image" of a region of the egg 14 as referred to herein means a set of parameter values that are associated with corresponding spatial regions within the egg 14 that correspond to pixels or voxels of the image. Each of the images shown in FIG. 5 consists of 64×64 voxels of a one voxel thick section through the egg, to which the corresponding parameter value T1 (left column), T2 (middle column) or diffusion coefficient D (right column) is associated and shown in gray scale in FIG. 5.

Herein, T1 denotes in the usual manner the time constant for the physical process responsible for the relaxation of the components of the nuclear spin magnetization vector parallel to the external magnetic field generated by the magnet arrangement 24, which is also referred to as the "longitudinal" or "spin-lattice relaxation time" in the art. It is hence the time it takes for the longitudinal magnetization to recover approximately 63% (1-(1/e)) of its initial value after being flipped into the magnetic transverse plane by a 90° radiofrequency pulse.

T2 denotes the "transverse" or "spin-spin relaxation time" and represents the decay constant for the component of the nuclear spin magnetization vector perpendicular to the external magnetic field generated by the magnet arrangement 24.

D is the molecular self diffusion coefficient (also referred to as "diffusion constant") of water molecules which was defined by A. Einstein in 1905 (A. Eistein in "Ann Physik", 17, p 549 (1905)). Unlike Fick's law, no "gradient" is needed for its definition. Instead, one may think of a certain small volume of water molecules within a large volume.

After wating a certain time interval t, a number of water molecules will "diffuse" outside of this volume due to Brownian Motion. The diffusion coefficient describes how fast this process is. The equation from Einstein describes the distance X for the water molecules travelling by Brownian Motion:

$$X^2 = 2 \cdot D \cdot t.$$

In NMR, this process can be measured using the water NMR Signal and the application of a magnetic field gradient. The diffusion coefficient D of water is changed by several anatomical details. For example, if there is a diffusion barrier, like a cell membrane, D will be decreased. This might happen when an embryo in an egg is developed with surrounding biological structures like blood vessel or the like.

Each of the 64×64 voxels therefore has three parameter values T1, T2 and D associated with it, and pairwise combinations of parameters associated with the same voxel are illustrated in the off-diagonal diagrams in FIG. 6. For example, in the lower left diagram, T1/D pairs for each voxel are indicated in a scatterplot, where T1/D pairs corresponding to an egg including a male embryo are represented by a cross and T1/D pairs corresponding to an egg including a female embryo are represented by a circle. Note that the spatial information, i.e. to which location within the egg a T1/D pair belongs cannot be seen in this diagram, but it is of course available. Similarly, the diagram in the left column, middle row shows T1/T2 pairs, and the diagram in the middle column, third row shows T2/D pairs, likewise represented by crosses and circles for male and female embryo containing eggs, respectively.

The other three off-diagonal diagrams show the same parameter combinations, but with the role of the horizontal and vertical axes interchanged, and presented in a manner where the sex is represented by black and gray color, which allows to better distinguish areas associated with male/female embryos by the naked eye.

The diagonal diagrams show histograms, where for each of the respective parameter bins, the number of voxels falling within the bin is counted. As can be seen from the three diagonal diagrams, for each of the three parameters T1, T2 and D, the histograms obtained for male and female embryo containing eggs differ. While the diagonal diagrams in FIG. 6 represent the histograms for measuring a single egg of each sex only, when averaging histograms for a plurality of eggs, as shown in FIGS. 7, 8 and 9, it can be seen that the deviations between the histograms are indeed systematic.

FIG. 7 shows an averaged histogram for the T1 values found in T1 images of 14 female and 12 male eggs. For both sexes, three peaks in T1 can be observed, where the two peaks at lower T1 times are practically identical for both sexes. However, male embryo containing eggs show a high T1 peak at about 2250 ms, while female embryo containing eggs show a high T1 peak at longer T1 times of about 2750 μs. The voxels of the T1 parameter image exhibiting these long T1 values are precisely the voxels located in the upper part of the egg, where the embryo is located. This can also be at least qualitatively seen from FIG. 5, where the eggs are shown in a horizontally lying configuration, and where the long T1 times are indeed found in the upper portion of each egg. The sex-related difference in the T1 high peak observed in regions close to the embryo can therefore be used to determine the sex of the embryo.

FIG. 8 is similar to FIG. 7, except that it shows an averaged histogram for the T2 values. The histogram shows two T2 peaks, where the high T2 peak corresponds to voxels in the upper part of the egg, and hence close to the embryo. For eggs with male embryo, the T2 high peak is again lower and located at about 150 ms, while the T2 high peak for eggs with female embryo is at about 200 ms. The difference between the T2 histograms, however, is not as pronounced as in case of T1.

Finally, FIG. 9 shows a similar histogram as FIGS. 7 and 8 for the diffusion coefficient, which is seen to exhibit three peaks. Again, the high diffusivity peak corresponds to voxels close to the embryo location, and its location is found to be dependent on sex. In particular, the high diffusivity peak for male embryo containing eggs is found to lie at around 1.75 mm²/s, while it is found to lie at around 2 mm²/s for female embryo containing eggs.

Since each of the parameters T1, T2 and D are sex sensitive, they can be used by the egg classification module 38 for determining the sex of the embryo contained within the egg. As was indicated above, for each of these parameters, a parameter value representative for a region of interest within the egg, i.e. at or close to the embryo location, can be determined and then be used in the sex determination by the classification module 38.

However, in preferred embodiments, the classification module 38 receives entire parameter images, such as the images shown in FIG. 5 and bases its determination thereon. For this purpose, the classification module 38 is preferably a machine learning module. A machine learning module is capable of learning from data and then making data-driven predictions or decisions through building a model from sample inputs. For example, as is suggested from FIG. 6, in the five-dimensional parameter space spanned by parameters T1, T2, D, x-coordinate and y-coordinate, there are obviously distinctions between male and female embryo eggs, and the pattern of this difference in this parameter space can be very well recognized by machine learning algorithms.

In machine learning and statistics, classification is the problem of identifying to which of a set of categories, in this case male and female, a new observation belongs, on the basis of a training set of data of observations whose category membership is known. A "classifier" is an algorithm or a machine that implements the classification.

Accordingly, in preferred embodiments, the classification module 38 is a machine learning module. Preferably, the NMR parameter values, or parameters derived therefrom, form feature values presented to the machine learning module as a feature vector.

In preferred embodiments, the classification module 38 is configured to determine the prediction of the sex of the embryo using a linear classifier. Linear classifiers classify objects by making a classification decision based on the value of a linear combination of the feature values. Suitable linear classifiers can be based on one or more of least square linear regression, nearest neighbors, logistic regression, and separating hyper planes. The theory of linear classifiers is known to the person skilled in the art of machine learning. For a detailed explanation of the above referenced linear classifiers, reference is made to Hastie, T., Tibshirani, R. & Friedman, J. *The Elements of Statistical Learning. Elements* 1, (Springer, 2009). An other suitable linear classifier is the so-called perceptron algorithm, which is an algorithm for supervised learning of binary classifiers. One of the advantages of the perceptron algorithm is that it allows for online learning, in that it processes elements in the training set one at a time. For further details of the perceptron algorithm, reference is made to Rosenblatt, F. *The perceptron: A*

*probabilistic model for information storage and organization in the brain. Psychol. Rev.* 65, 386-408 (1958).

In alternative embodiments, the classification module 38 is configured to determine the prediction of the sex of the embryo using a nonlinear classifier. For the determination of embryo sex using the above NMR parameters as feature values, nonlinear classifiers based on piecewise polynomials, splines, kernel smoothing, tree-based methods, support vector machines, boosting, additive and ensemble methods or graph models may be advantageously employed. Again, a detailed explanation of these nonlinear classifiers can be taken from the above work by Hustle, which is incorporated herein by reference. A particularly suitable nonlinear classifier is based on the random forest method, that operates by constructing a multitude of decision trees at training time and outputting the class that is the so-called mode of the classes of decision trees. For more details on the random forest method, reference is made to Criminisi, A. *Decision Forests: A Unified Framework for Classification, Regression, Density Estimation, Manifold Learning and Semi-Supervised Learning. Foundations and Trends® in Computer Graphics and Vision* 7, 81-227 (2011).

In yet alternative embodiments, the classification module 38 is configured to determine the prediction of the sex of the embryo using a deep learning algorithm. Deep learning is part of the broad family of machining learning methods as referred to in the present disclosure, and is based on learning data representations, as opposed to task specific algorithms. For a review of suitable deep learning algorithms, reference is made to Y., L., Y., B. & G., H. *Deep learning. Nature* 521, 436-444 (2015). Particularly suitable deep learning algorithms for the purposes of the present invention are based on convolutional neural networks, as described in Le Cun, Y. et al. *Handwritten Digit Recognition with a Back-Propagation Network. Adv. Neural Inf. Process. Syst.* 396-404 (1990). doi:w.iiii/dsu.12130, based on recurrent neural networks, as described in Donahue, J. et al. *Long-term Recurrent Convolutional Networks for Visual Recognition and Description. Cvpr* 07-12 June, 2625-2634 (2015), or based on long short-term memory networks, as described in Hochreiter, S. & Schmidhuber, J. *Long Short-Term Memory. Neural Comput.* 9, 1735-1780 (1997).

The currently preferred implementation of a machine learning classifier for egg sexing is based on convolutional neural networks (CNN). FIG. 14 schematically shows a general implementation of the architecture. C parameter images of M×N pixels are shown to the CNN. It applies C1 m×n convolutional filters, pooling and activation over the input, resulting in a first layer of size M1×N1 with C1 channels. This process is repeated p times until the features of interest of the parameter maps are extracted. Then, q neural layers of L channels are interconnected to give a final probability for a male or a female.

Implementations of these CNN may include variations of the convoluting filters, pooling, non-linear activation, or the architecture. Examples are, among others, AlexNet (Krizhevsky, A., Sutskever, I. & Hinton, G. E. *ImageNet Classification with Deep Convolutional Neural Networks. Adv. Neural Inf. Process. Syst.* 1-9 (2012). doi:http://dx.doi.org/10.1016/j.protcy.2014.09.007), Overfeat (Sermanet, P. et al. *OverFeat: Integrated Recognition, Localization and Detection using Convolutional Networks. arXiv Prepr. arXiv* 1312.6229 (2013). doi:10.1109/CVPR.2015.7299176), VGG (Simonyan, K & Zisserman, A. *Very Deep Convolutional Networks for Large-Scale Image Recognition. Int. Conf. Learn. Represent.* 1-14 (2015). doi:10.1016/j.infsof.2008.09.005), Network-in-network (NiN) (Lin, M, Chen, Q. & Yan, S. *Network In Network. arXiv Prepr.* 10 (2013). doi:10.1109/ASRU.2015.7404828), GoogLeNet and Inception (Szegedy, C. et al. *Going deeper with convolutions. in Proceedings of the IEEE Computer Society Conference on Computer Vision and Pattern Recognition* 07-12 Jun., 1-9 (2015)), ResNet (He, K, Zhang, X., Ren, S. & Sun, J. *Deep Residual Learning for Image Recognition.* in 2016 *IEEE Conference on Computer Vision and Pattern Recognition (CVPR)* 770-778 (2016). doi:10.1109/CVPR.2016.90), SqueezeNet (Iandola, F. N. et al. SQUEEZENET:ALEXNET-LEVEL ACCURACY WITH 50XFEWERPARAMETERSAND <0.5 MB MODEL SIZE. arXiv 1-5 (2016). doi:10.1007/978-3-319-24553-9), and ENet (Paszke, A., Chaurasia, A., Kim, S. & Culurciello, E. *ENet: A Deep Neural Network Architecture for Real-Time Semantic Segmentation. arXiv* 1-10 (2016)).

According to the present understanding, the above three NMR parameters T1, T2 and D are the most relevant for sex prediction, and the most reliable results can be obtained if the classification module 38 bases its prediction on all three parameters, in particular parameter images. However, the invention is not limited to this. In some embodiments, a set of two or more NMR parameters is employed, of which at least one is selected from said group consisting of a T1 relaxation time, a T2 relaxation time and a diffusion coefficient. In such embodiments, the set of NMR parameters may further comprise one or more of the following parameters: a T2* relaxation time, a T1ρ relaxation time, and a spin density associated with one or more of the nuclei 1H, 13C, 23Na, and 31P.

In addition or alternatively, the set of NMR parameters may further comprise one or more of a chemical shift signal of metabolites, in particular water, lipids, amino acids, nucleic acids, or hormones; a chemical shift selective transfer signal; and zero quantum coherence or multiple quantum coherence NMR signals.

Instead of distinguishing between the sex of embryos in an egg 14, the apparatus 10 of FIG. 1 can be operated for determining the fertility of an egg 14, as will be explained next with reference to FIGS. 10 to 12.

FIG. 10 shows an averaged histogram of the diffusion coefficient observed throughout a plurality of fertile eggs (solid line) and infertile eggs (broken line). More precisely, diffusion coefficients have been determined for each of the voxels of a diffusion coefficient image of the entire volume of a plurality of eggs. As is seen from FIG. 10, the histogram has very similar values around 2 mm$^2$/s (corresponding to the albumin), but diffusion coefficients around 1 mm$^2$/s (found in regions within the yolk) are more frequently found in infertile eggs than infertile eggs. Accordingly, this difference can be taken as a criterion to determine the fertility.

FIG. 11 shows a scatterplot of pairs of diffusion coefficient histogram values at 1 mm$^2$/s and 2 mm$^2$/s, for nine fertile eggs and ten infertile eggs. As can be seen from FIG. 11, in the simple scatterplot, all but one egg of each species is located on a corresponding side of a dashed separation line, which denotes a ratio of the histogram values at 2 and 1 mm$^2$/s, which ratio is generally exceeded for fertile eggs and not reached for infertile eggs.

FIG. 12 shows an NMR spectrum of the yolk for fertile and infertile eggs. The spectrum shows a peak at about 1 ppm corresponding to fat and a peek at about 4.7 ppm corresponding to water. The inventors have found that the ratio in the height of the fat peak to the height of the water peak is higher for infertile eggs than for fertile eggs.

Accordingly, based on this ratio, the distinction between fertile and infertile eggs can likewise be made.

In preferred embodiments, the two indicators for fertility, i.e. the shape of the diffusion coefficient histogram and the ratio of the fat and water peaks, can be combined to increase the reliability of the prediction. Note that the comparison of the histogram values at 1 mm²/s and 2 mm²/s is only one way of exploiting the characteristic shape of the diffusion coefficient histogram. In preferred embodiments, the entire diffusion coefficient histogram may be presented to a machine learning algorithm, which automatically learns to distinguish between diffusion coefficient histograms corresponding to fertile and infertile eggs. FIG. 11 indicates that there is enough fertility related information in the diffusivity histogram to make the correct distinction, which can then be properly accounted for by a machine learning module, such as a suitably configured egg classification module 38.

Similarly, while the ratio of the fat and water peaks in the spectrum of FIG. 12 is only one way to distinguish the fertility of the egg based on the spectrum, in alternative embodiments, the entire spectrum could be presented to a machine learning module, such as a suitably configured egg classification module 38, which after sufficient training could distinguish between fertile and infertile eggs based on the spectrum.

Note further that the distinguishing between fertile and infertile eggs 14 can be carried out with the same apparatus 10 as shown in FIG. 1, where the only difference is the NMR measurement protocol, which is provided by the central controller 44 to the components of the NMR apparatus 18, such as to measure the parameters of interest, and the algorithm employed by the egg classification module 38.

FIG. 13 shows a simplified apparatus 10' which has the same functionality as the apparatus 10 of FIG. 1, except that it is not devised for high throughput automated determination of sex or fertility. The apparatus 10' comprises an NMR apparatus 18, which basically includes the same type of components as the apparatus 10 of FIG. 1, but is devised for measuring a single egg only. The simplified apparatus of FIG. 13 does not include a conveying device 12, and likewise lacks and egg sorting device 40. Instead, the output of the egg classification module 38 is presented to a user interface 60. This simplified version can be used for laboratory scale analysis, rather than industrial analysis. While preferred embodiments of the invention aim at high throughput automated methods and apparatuses including a conveying device 12 and egg sorting device 40, and aim at carrying out measurements on a plurality of eggs 14 in parallel, the invention is not limited to this, and all of the embodiments described herein may likewise apply to apparatuses dispensing with conveying device 12 and egg sorting device 40.

Although a preferred exemplary embodiment is shown and specified in detail in the drawings and the preceding specification, these should be viewed as purely exemplary and not as limiting the invention. It is noted in this regard that only the preferred exemplary embodiment is shown and specified, and all variations and modifications should be protected that presently or in the future lie within the scope of protection of the invention as defined in the claims.

LIST OF REFERENCES 10 apparatus for noninvasive determining the sex of an embryo or the fertility of an egg
12 conveying device
14 egg
16 tray
18 NMR apparatus
20 conveyor belt
22 transport controller
24 magnet arrangement
26 gradient coils
28 gradient controller
30 RF coil array
30a RF coil
32 RF controller
34 RF detector
36 image reconstruction module
38 egg classification module
40 egg sorting device
42 suction cup of egg sorting device 40
44 central controller
45 data channel
46 transport direction
48 dimple in tray 16
50 antenna section
52 tuning capacitor
54 preamplifier
56 transmission lines
58 NMR spectrometer
60 user interface

The invention claimed is:

1. A method of automated noninvasive determining the sex of an embryo of a bird's egg, comprising the following steps:
   conveying a plurality of bird eggs sequentially or in parallel into an NMR apparatus, subjecting the bird eggs to an NMR measurement, and determining, for each of said eggs, one or more NMR parameter value images of a region of said egg, in which NMR parameter values are associated with corresponding pixels or voxels of the image, wherein said one or more NMR parameters are selected from the group consisting of a T1 relaxation time, a T2 relaxation time and a diffusion coefficient,
   forwarding said one or more NMR parameter value images, or images of parameters derived therefrom, to a classification module, said classification module configured for determining, based on said one or more NMR parameter value images, or images of parameters derived therefrom, a prediction of the sex of the embryo of the associated egg, and
   conveying said plurality of bird eggs out of said NMR apparatus and sorting the eggs according to the sex prediction provided by said classification module.

2. The method of claim 1, wherein said one or more NMR parameters comprise a set of two or more NMR parameters, of which at least one is selected from said group consisting of a T1 relaxation time, a T2 relaxation time and a diffusion coefficient.

3. The method of claim 2, wherein said set of NMR parameters preferably further comprises one or more of the following parameters: a T2* relaxation time, a T1ρ relaxation time, and a spin density associated with one or more of the nuclei 1H, 13C, 23Na, and 31P.

4. The method of claim 1, wherein said classification module is a machine learning module.

5. The method of claim 1, wherein said classification module is configured to determine the prediction of the sex of the embryo using a linear classifier, said linear classifier being based on one or more of least square linear regression, nearest neighbors, logistic regression, separating hyper planes or perceptrons.

6. The method claim 1, wherein said classification module is configured to determine the prediction of the sex of the embryo using a nonlinear classifier in particular a nonlinear classifier based on one of piecewise polynomials, splines, kernel smoothing, tree-based methods, support vector machines, random forest, boosting, additive and ensemble methods and graph models.

7. The method of claim 1, wherein said classification module is configured to determine the prediction of the sex of the embryo using a deep learning algorithm in particular a deep learning algorithm based on one of convolutional neural networks, recurrent neural networks and long short-term memory networks.

8. The method of claim 1, wherein the NMR measurement comprises NMR imaging, wherein an NMR imaging plane is arranged such as to intersect the location of the embryo.

9. The method of claim 1, wherein said method is carried out prior to the eighth day of breeding, preferably on the fifth day of breeding.

10. The method of claim 1, wherein said eggs are arranged in a regular pattern, in particular in a matrix configuration, on a tray during said conveying and NMR measurement, wherein preferably the number of eggs arranged on said tray is at least 36, preferably at least 50 and most preferably at least 120.

11. The method of claim 10, wherein said NMR apparatus preferably comprises an array of RF coils for applying RF magnetic fields to the eggs located on the tray and/or for detecting NMR signals, said array of RF coils comprising one or more of
 a plurality of coils arranged in a plane located above the tray loaded with eggs when conveyed to the NMR apparatus,
 a plurality of coils arranged in a plane located underneath the tray loaded with eggs when conveyed to the NMR apparatus,
 a plurality of coils arranged in vertical planes extending between rows of eggs on the tray when conveyed to the NMR apparatus, which rows extend in parallel with the conveying direction of the tray into and out of the NMR apparatus.

12. An apparatus for automated noninvasive determining the sex of an embryo of a bird's egg, comprising:
 an NMR apparatus,
 a conveying device for conveying a plurality of bird eggs sequentially or in parallel into said NMR apparatus and out of said NMR apparatus,
 wherein said NMR apparatus is configured for subjecting the bird eggs to an NMR measurement, to thereby determine, for each of said eggs, one or more NMR parameter value images of a region of said egg, in which NMR parameter values are associated with corresponding pixels or voxels of the image, wherein said one or more NMR parameters are selected from the group consisting of a T1 relaxation time, a T2 relaxation time and a diffusion coefficient,
 wherein said apparatus further comprises a classification module configured to receive said one or more NMR parameter value images, or images of parameters derived therefrom, said classification module configured for determining, based on said one or more NMR parameter value images or images of parameters derived therefrom, a prediction of the sex of the embryo of the associated egg, and an egg sorting device for sorting the eggs according to the sex prediction provided by said classification module.

13. The apparatus of claim 12, wherein said one or more NMR parameters comprise a set of two or more NMR parameters, of which at least one is selected from said group consisting of a T1 relaxation time, a T2 relaxation time and a diffusion coefficient.

14. The apparatus of claim 13, wherein said set of NMR parameters preferably further comprises one or more of the following parameters: a T2* relaxation time, a T1ρ relaxation time, and a spin density associated with one or more of the nuclei 1H, 13C, 23Na, and 31P.

15. The apparatus of claim 12, wherein said classification module is a machine learning module.

16. The apparatus of claim 12, wherein said classification module is preferably configured to determine the prediction of the sex of the embryo using a linear classifier, in particular a linear classifier based on one or more of least square linear regression, nearest neighbors, logistic regression, separating hyper planes and perceptrons.

17. The apparatus of claim 12, wherein said classification module is preferably configured to determine the prediction of the sex of the embryo using a nonlinear classifier, in particular a nonlinear classifier based on one of piecewise polynomials, splines, kernel smoothing, tree-based methods, support vector machines, random forest, boosting, additive and ensemble methods and graph models.

18. The apparatus of claim 12, wherein said classification module is preferably configured to determine the prediction of the sex of the embryo using a deep learning algorithm, in particular a deep learning algorithm based on one of convolutional neural networks, recurrent neural networks or long short-term memory networks.

19. The apparatus of claim 12, further comprising a tray on which said eggs can be arranged in a regular pattern, in particular in a matrix configuration, during said conveying and NMR measurement, wherein the number of eggs that can be arranged on said tray is preferably at least 36, more preferably at least 50 and most preferably at least 120.

20. The apparatus of claim 19, wherein said NMR apparatus comprises an array of RF coils for one of applying RF magnetic fields to the eggs located on the tray and detecting NMR signals, said array of RF coils comprising one or more of
 a plurality of coils arranged in a plane located above the tray loaded with eggs when conveyed to the NMR apparatus,
 a plurality of coils arranged in a plane located underneath the tray loaded with eggs when conveyed to the NMR apparatus,
 a plurality of coils arranged in vertical planes extending between rows of eggs on the tray when conveyed to the NMR apparatus, which rows extend in parallel with the conveying direction of the tray into and out of the NMR apparatus.

21. The apparatus of claim 20, wherein the plurality of coils is arranged in a plane located above or underneath the tray loaded with eggs and the ratio of the number of coils to the number of eggs arranged on said tray is between 1:1 and 1:16.

22. The apparatus of claim 19, wherein said NMR apparatus comprises an array of RF coils for one or both of applying RF magnetic fields to the eggs located on the tray and detecting NMR signals, said array of RF coils being integrated with or attached to said tray.

23. The apparatus of claim 22, wherein the tray preferably comprises a plurality of dimples or pockets for receiving a corresponding egg, and wherein a number of coils is associated with each of said dimples or pockets, wherein said number of coils per dimple or pocket is at least 2.

* * * * *